United States Patent [19]
Kojima et al.

[11] Patent Number: 5,989,875
[45] Date of Patent: *Nov. 23, 1999

[54] METHOD OF PROCESS FOR PRODUCING L-LYSINE BY FERMENTATION

[75] Inventors: Hiroyuki Kojima; Yuri Ogawa; Kazue Kawamura; Konosuke Sano, all of Kawasaki, Japan

[73] Assignee: Ajinomoto Co., Inc., Tokyo, Japan

[ * ] Notice: This patent is subject to a terminal disclaimer.

[21] Appl. No.: 08/973,461

[22] PCT Filed: Mar. 14, 1996

[86] PCT No.: PCT/JP96/00648

§ 371 Date: Apr. 20, 1998

§ 102(e) Date: Apr. 20, 1998

[87] PCT Pub. No.: WO96/41871

PCT Pub. Date: Dec. 27, 1996

[30] Foreign Application Priority Data

Jun. 13, 1995 [JP] Japan ................................ 7-146054

[51] Int. Cl.$^6$ ............................. C12N 15/00; C12N 9/88; C12N 9/12
[52] U.S. Cl. ................. 435/115; 435/252.3; 435/252.31; 435/232; 435/194
[58] Field of Search ...................... 435/115, 232, 435/252.3, 252.31, 194

[56] References Cited

U.S. PATENT DOCUMENTS 5,258,300  11/1993  Glassman et al. .................... 435/240.4
5,545,545   8/1996  Gengenbach et al. ............... 435/172.3

FOREIGN PATENT DOCUMENTS

93/19190  9/1993  WIPO .
94/11517  5/1994  WIPO .
95/16042  6/1995  WIPO .

OTHER PUBLICATIONS

Sugita T, et al. Cloning and characterization of the mutated threonine operon (thrA(1)5A(2)5BC) of Serratia marcescens. Gene. May 1, 1987; 57(2–3): 151–158.

Primary Examiner—Robert A. Wax
Assistant Examiner—Bradley S. Mayhew
Attorney, Agent, or Firm—Oblon, Spivak, McClelland, Maier & Neustadt, P.C.

[57] ABSTRACT

A bacterium belonging to the genus Serratia, which is transformed by introducing into its cells, a DNA coding for a dihydrodipicolinate synthase originating from a bacterium belonging to the genus Escherichia or Serratia having mutation to desensitize feedback inhibition by L-lysine and a DNA coding for an aspartokinase originating from a bacterium belonging to the genus Escherichia or Serratia having mutation to desensitize feedback inhibition by L-lysine is cultivated in an appropriate medium, L-lysine is produced and accumulated in a culture thereof, and L-lysine is collected from the culture.

14 Claims, 9 Drawing Sheets

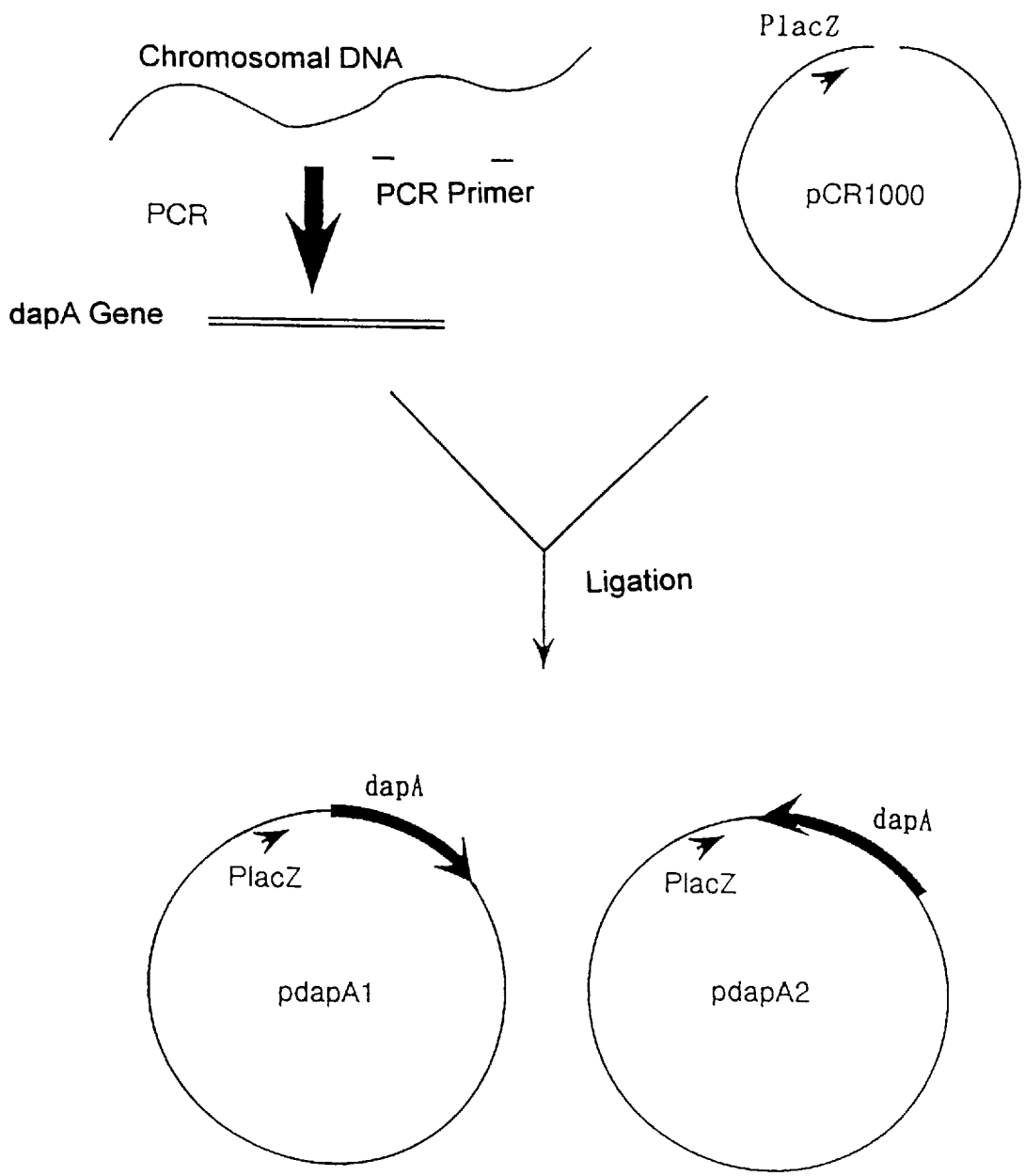
F I G. 1

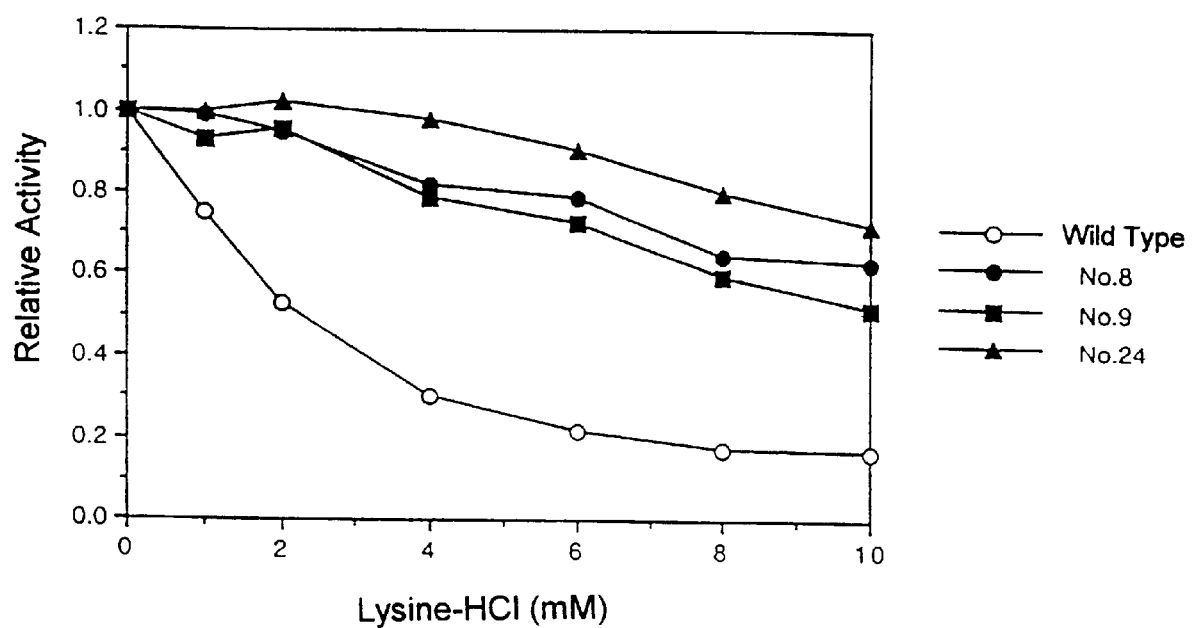
F I G. 2

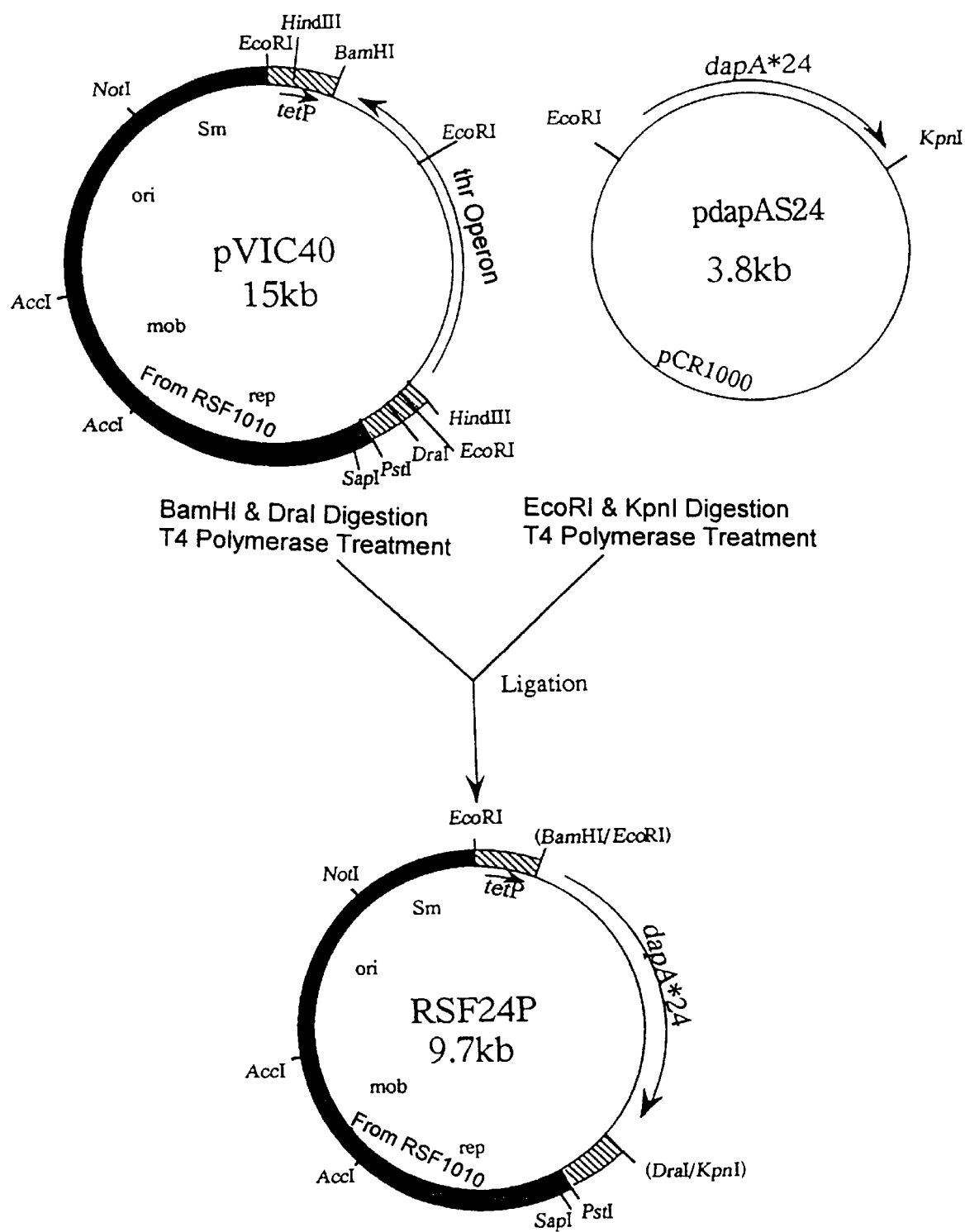
F I G. 7

METHOD OF PROCESS FOR PRODUCING L-LYSINE BY FERMENTATION

TECHNICAL FIELD

The present invention relates to microbial industry, and in particular relates to a method of producing L-lysine by fermentation, DNA's and microorganisms to be used for this production method.

BACKGROUND ART

In the prior art, when L-lysine is produced by a fermentative method, a microbial strain separated from the natural environment or an artificial mutant strain obtained from such a microbial strain is used in order to improve the productivity. A large number of artificial mutant strains producing L-lysine are known. Most of them are S-2-aminoethylcysteine (AEC) resistant mutant strains, and belong to the genus of Brevibacterium, Corynebacterium, Bacillus, Escherichia or Serratia. Further, various techniques have been disclosed for increasing amino acid production, for example, by employing a transformant using recombinant DNA (U.S. Pat. No. 4,278,765).

For example, bacteria belonging to the genus Serratia are widely used as bacteria producing various amino acids such as L-proline, L-histidine, L-arginine, L-threonine, L-valine and L-isoleucine and have excellent properties as amino acid-producing bacteria in various aspects, as described in "Oyo Bunshi Idengaku (Applied Molecular Genetics)" publihed by Kodansha Scientific, 1986, ISBN4-06-139659-5) and "Aminosan Hakko (Amino Acid Fermentation)" published by Gakkai Shuppan Center, 1986, ISBN4-7622-9454-3). Production of various amino acids by using bactria belonging to the genus Serratia has been reported. According to one report (Japanese Patent Publication No. 51-9393 (1976)) which reported that it became L-lysine-productive, a yield (a value given by dividing a concentration of produced L-lysine HCl salt by an initial concentration of a carbon source) is calculated at 5.4%.

*Serratia marcescens*, which is a representative strain of bacteria belonging to the genus Seratia, is similar to bacteria belonging to the genus Escherichia in its gene structure and mechanism of gene expression and regulation, and a cloning vector usable for recombination of DNA in bacteria belonging to the genus Eschrichia can be used for the bacteria belonging to the genus Serratia (Japanese Patent Application Laid-Open Nos. 2-27980 (1990) and 5-10076 (1993)).

By the way, the dihydrodipicolinate synthase (DDPS) is an enzyme for dehydrating and condensing aspartosemialdehyde and pyruvic acid to synthesize dihydrodipicolinic acid. This reaction is located at an entrance into a branch to proceed to an L-lysine biosynthesis system in biosynthesis of amino acids of the aspartic acid family. This enzyme is known to be in charge of an important regulatory site of the L-lysine biosynthesis as aspartokinase is in bacteria belonging to the genus Escherichia.

DDPS is encoded by a gene called dapA in *E. coli* (*Escherichia coli*). The dapA has been cloned, and its base sequence has been also determined (Richaud, F. et al., *J. Bacteriol.*, 297 (1986)).

On the other hand, aspartokinase (hereinafter sometimes abbreviated as "AK") is an enzyme for catalyzing a reaction to convert aspartic acid into β-phosphoaspartic acid, which serves as a main regulatory enzyme in a biosynthesis system of amino acids of the aspartic acid family. AK of *E. coli* has three types (AKI, AKII, AKIII), two of which are complex enzymes with homoserine dehydrogenase (hereinafter sometimes abbreviated as "HD"). One of the complex enzymes is AKI-HDI encoded by a thrA gene, and the other is AKII-HDII encoded by a metLM gene. AKI is subjected to concerted suppression by threonine and isoleucine and inhibited by threonine, while AKII is suppressed by methionine.

On the contrary, it is known that only AKIII is a simple function enzyme, which is a product of a gene designated as lysC, and is subjected to suppression and feedback inhibition by L-lysine. The ratio of their intracellular activities is AKI:AKII:AKIII=about 5:1:4.

DDPS and AKIII are subjected to feedback inhibition by L-lysine as described above, and it hinders effective production of L-lysine. It is expected that L-lysine can be efficiently produced by fermentation by using a bacterium belonging to the genus Serratia if a mutant enzyme of DDPS or AKIII, which is not subjected to feedback inhibition by L-lysine, can be obtained. However, there is no preceding literature which describes such a mutant enzyme of DDPS, and although there is one report on a mutant enzyme of AKIII (Boy, E., et al., J. Bacteriol., 112, 84 (1972)), no example has been known which suggests that such a mutant enzyme may improve productivity of L-lysine. In addition, they have not been known with respect to genes of an L-lysine biosynthesis system of bacteria belonging to the genus Serratia.

DISCLOSURE OF THE INVENTION

The present invention has been made taking the aforementioned viewpoints into consideration, an object of which is to obtain DDPS and AK, especially, DDPS and AKIII originating from bacteria belonging to the genus Serratia with sufficiently desensitized feedback inhibition by L-lysine, and provide a method of producing L-lysine by using a bacterium belonging to the genus Serratia, which is more efficient than those in the prior art.

As a result of diligent and repeated investigation in order to achieve the object described above, the present inventors have succeeded in obtaining DNA coding for DDPS originating from a bacterium belonging to the genus Escherichia in which feedback inhibition by L-lysine is sufficiently desensitized. The DNA coding for DDPS originating from *E. coli* in which feedback inhibition by L-lysine is sufficiently desensitized is sometimes referred to herein as mutant dapA or dapA*.

The inventors have further created a bacterium belonging to the genus Serratia harboring and aspartokinase in which feedback inhibition by L-lysine is desensitized and DDPS in which feed back inhibition by L-lysine is sufficiently desensitized. The DNA coding for aspartokinase originating from *E. coli* in which feedback inhibition by L-lysine is sufficiently desensitized is sometimes referred to herein as mutant lysC or lysC*.

The inventors have further created a bacterium belonging to the genus Serratia harboring mutant dapA and mutant lysC. And it has been found that a considerable amount of L-lysine can be produced and accumulated in a culture by cultivating the aforementioned bacterium belonging to the genus Serratia in an appropriate medium.

Namely, the present invention provides a bacterium belonging to the genus Serratia, which is transformed by introduing into its cells, a DNA coding for a dihydrodipicolinate synthase having mutation to desensitize feedback inhibition by L-lysine. The dihydrodipicolinate synthase is exemplified by that originating from a bacterium belonging to the genus Escherichia. With respect to the dihydrodipicolinate synthase originating from the bacterium belonging to the genus Escherichia, the mutation to desensitize feedback inhibition by L-lysine is exemplified by mutation to replace an 81st alanine residue with a valine residue, mutation to replace a 118th histidine residue with a tyrosine residue, and mutation to replace the 81st alanine residue with the valine residue and replace the 118th histidine residue with the tyrosine residue, as counted from the N-terminal in an amino acid sequence of dihydrodipicolinate synthase defined in SEQ ID NO:4 in Sequence Listing. The dihydropicolinate synthase may be one native to a bacterium belonging to the genus Serratia provided that it has mutation to desensitize feedback inhibition by L-lysine.

The present invention further provides the aforementioned bacterium belonging to the genus Serratia harboring an aspartokinase in which feedback inhibition by L-lysine is desensitized. A method to allow the bacterium belonging to the genus Serratia to harbor the aspartokinase in which feedback inhibition by L-lysine is desensitized is exemplified by a method for introducing into its cells, a DNA coding for an aspartokinase III originating from a bacterium belonging to the genus Escherichia having mutation to desensitize feedback inhibition by L-lysine.

The mutation of the aspartokinase III originating from a bacterium belonging to the genus Escherichia to desensitize feedback inhibition by L-lysine is exemplified by mutation to replace a 323rd glycine residue with an aspartic acid residue, mutation to replace the 323rd glycine residue with the aspartic acid residue and replace a 408th glycine residue with an aspartic acid residue, mutation to replace a 34th arginine residue with a cysteine residue and replace the 323rd glycine residue with the aspartic acid residue, mutation to replace a 325th leucine residue with a phenylalanine residue, mutation to replace a 318th methionine residue with an isoleucine residue, mutation to replace the 318th methionine residue with the isoleucine residue and replace a 349th valine residue with a methionine residue, mutation to replace a 345th serine residue with a leucine residue, mutation to replace a 347th valine residue with a methionine residue, mutation to replace a 352nd threonine residue with an isoleucine residue, mutation to replace the 352nd threonine residue with the isoleucine residue and replace a 369th serine residue with a phenylalanine residue, mutation to replace a 164th glutamic acid residue with a lysine residue, and mutation to replace a 417th methionine residue with an isoleucine residue and replace a 419th cysteine residue with a tyrosine residue, as counted from the N-terminal in an amino acid sequence of aspartokinase III defined in SEQ ID NO:8 in Sequence Listing.

Needless to say, the aspartokinase in which feedback inhibition by L-lysine is densensitized may be one native to a bacterium belonging to the genus Serratia.

The DNA coding for a dihydrodipicolinate synthase having mutation to desensitize feedback inhibition by L-lysine, and the DNA coding for an aspartokinase having mutation to desensitize feedback inhibition by L-lysine may be each harbored in cells of a bacterium belonging to the genus Serratia on an identical plasmid or separate plasmids.

The bacterium belonging to the genus Serratia, to which a DNA coding for the dihydrodipicolate synthase having mutation to desensitize feedback inhibition by L-lysine, is exemplified by a bacterium which is deficient in lysine decarboxylase.

The present invention further provides a method of producing L-lysine comprising the steps of cultivating any of the bacteria belonging to the genus Serratia described above in an appropriate medium, producing and accumulating L-lysine in a culture thereof, and collecting L-lysine from the culture.

In this specification, DNA coding for DDPS or AKIII, or DNA containing a promoter in addition thereto is sometimes referred to as "DDPS gene" or "AKIII gene". Further, the mutant enzyme is which feedback inhibition by L-lysine is desensitized, and DNA coding for it or DNA containing a promoter in addition to it are sometimes simply referred to as "mutant enzyme" and "mutant gene", respectively. Further, the phrase "feedback inhibition by L-lysine is desensitized" means that substantial desensitization of inhibition is sufficient, and complete desensitization is not necessary.

The present invention will be explained in detail below.
<1> DNA coding for mutant dihydrodipicolinate synthase (DDPS) used for the method of the present invention The DNA coding for the mutant DDPS used for the method of the present invention has mutation to desensitize feedback inhibition by L-lysine of DDPS encoded in DNA coding for the wild type DDPS. DDPS is exemplified by those originating from bacteria belonging to the genus Escherichia, especially DDPS originating from *E. coli*. Further, any DDPS of bacteria belonging to the genus Serratia may be also used provided that it has mutation to desensitize feedback inhibition by L-lysine. The mutation of DDPS originating from a bacterium belonging to the genus Escherichia to desensitize feedback inhibition by L-lysine is exemplified by:

(1) mutation to replace an 81st alanine residue with a valine residue;

(2) mutation to replace a 118th histidine residue with a tyrosine residue; and (3) mutation to replace the 81st alanine residue with the valine residue and replace the 118th histidine residue with the tyrosine residue;

as counted from the N-terminal of DDPS in an amino acid sequence of DDPS defined in SEQ ID NO:4 in Sequence Listing.

The DNA coding for the wild type DDPS is not especially limited provided that it codes for DDPS originating from a bacterium belonging to the genus Escherichia or Serratia. The DNA coding for DDPS originating from a bacterium belonging to the genus Escherichia is concretely exemplified by DNA coding for an amino acid sequence defined in SEQ ID NO:4, and is further concretely exemplified by DNA of a sequence represented by base numbers 272–1147 in a base sequence defined in SEQ ID NO:3. In these sequences, those having the mutation in base sequence to cause the replacement of amino acid residues described above are examples of the DNA coding for the mutant DDPS used for the present invention. Any codon corresponding to the replaced amino acid residue is available especially irrelevantly to its kind, provided that it codes for the identical amino acid residue. Further, it is postulated that possessed DDPS is slightly different in sequence depending on difference in bacterial species and bacterial strain, however, those having replacement, deletion or insertion of amino acid residue(s) at position(s) irrelevant to enzyme activity are also included in the mutant DDPS gene of the present invention.

A method for obtaining such a mutant gene may be as follows. At first, a DNA containing a wild type DDPS gene or DDPS gene having a mutation which substantially has no adverse effect on enzyme activity of DDPS is subjected to an in vitro mutation treatment, and a DNA after the mutation treatment is ligated with a vector DNA adapted to a host to obtain a recombinant DNA. The recombinant DNA is introduced into a host microorganism to obtain transformants. When one which expresses a mutant DDPS is selected among the aforementioned transformants, such a transformant harbors a mutant gene. Alternatively, a DNA containing a wild type DDPS gene or DDPS gene having another mutation may be ligated with a vector DNA adapted to a host to obtain a recombinant DNA. The recombinant DNA is thereafter subjected to an in vitro mutation treatment, and a recombinant DNA after the mutation treatment is introduced into a host microorganism to obtain transformants. When one which expresses a mutant DDPS is selected among the aforementioned transformants, such a transformant also harbors a mutant gene.

It is also acceptable that a microorganism which produces a wild type enzyme is subjected to a mutation treatment to create a mutant strain which produces a mutant enzyme, and then a mutant gene is obtained from the mutant strain. Alternatively, a transformant to which a recombinant DNA ligated with a wild type gene is introduced may be subjected to a mutation treatment to create a mutant strain which produces a mutant enzyme. When a recombinant DNA is thereafter recovered from the mutant strain, a mutant gene is created on the aforementioned DNA.

The agent for performing the in vitro mutation treatment of DNA is exemplified by hydroxylamine and the like. Hydroxylamine is a chemical mutation treatment agent which causes mutation from cytosine to thymine by changing cytosine to $N^4$-hydroxycytosine. Alternatively, when a microorganism itself is subjected to a mutation treatment, the treatment is performed by using ultraviolet light irradiation, or a mutating agent usually used for artificial mutation such as N-methyl-N'-nitro-N-nitrosoguanidine (NTG) or nitrous acid.

As a donor microorganism for DNA containing the wild type DDPS gene or DDPS gene having another mutation described above, any one including a microorganism belonging to the genus Escherichia or Serratia can be used. Concretely, as the microorganism belonging to the genus Eschericha, it is possible to utilize those described in a book written by Neidhardt et al. (Neidhardt, F. C. et al., *Escherichia coli* and *Salmonella typhimurium,* American Society for Microbiology, Washington D.C., 1208, table 1). For example, an *E. coli* JM109 strain and an MC1061 strain are mentioned. When a wild strain is used as a donor microorganism for DNA containing a DDPS gene, a DNA containing a wild type DDPS gene can be obtained.

On the other hand, the microorganism belonging to the genus Serratia is exemplified by *Seratia marcescens,* for example, *Seratia marcescens* AJ13125 strain (FERM BP-5441).

(1) Preparation of wild type DDPS gene

An example of preparation of DNA containing a DDPS gene will be described below. The preparation is described herein with respect to *E. coli,* and the DDPS gene may be similarly prepared with respect to another bacterium belonging to the genus Escherichia and a bacterium belonging to the genus Serratia.

At first, *E. coli* having wild type dapA, for example, MC1061 strain, is cultivated to obtain a culture. When the microorganism described above is cultivated, cultivation may be performed in accordance with an ordinary solid culture method, however, cultivation is preferably performed by adopting a liquid culture method considering efficiency during collection of the bacterium. A medium may be used in which one or more nitrogen sources such as yeast extract, peptone, meat extract, corn steep liquor and exudate of soybean or wheat are added with one or more inorganic salts such as potassium dihydrogenphosphate, dipotassium hydrogenphosphate, magnesium sulfate, sodium chloride, magnesium chloride, ferric chloride, ferric sulfate or manganese sulfate, and further optionally and adequately with sugar materials, vitamins and the like. It is appropriate that the initial pH of the medium is adjusted to 6 to 8. The cultivation may be performed for 4 to 24 hours at 30 to 42° C., preferably at about 37° C. by means of deep culture with aeration and agitation, shaking culture or stationary culture or the like.

The culture thus obtained is centrifuged, for example, at 3,000 r.p.m. for 5 minutes to obtain a cell pellet of *E. coli* MC1061 strain. Chromosomal DNA can be obtained from the cell pellet by means of, for example, a method of Saito and Miura (*Biochem. Biophys. Acta.,* 72, 619 (1963)), or a method of K. S. Kirby (*Biochem. J.,* 64, 405 (1956)).

In order to isolate the DDPS gene from the chromosomal DNA thus obtained, a chromosomal DNA library is prepared. At first, the chromosomal DNA is partially digested with a suitable restriction enzyme to obtain a mixture of various fragments. A wide variety of restriction enzymes can be used if the degree of cutting is controlled by the cutting reaction time and the like. For example, Sau3I is allowed to react on the chromosomal DNA at a temperature not less than 30° C., preferably at 37° C. at an enzyme concentration of 1 to 10 units/ml for various periods of time (1 minute to 2 hours) to digest it.

Next, obtained DNA fragments are ligated with a vector DNA autonomously replicable in cells of bacteria belonging to the genus Escherichia to prepare recombinant DNA. Concretely, a restriction enzyme, which generates the terminal base sequence complementary to that generated by the restriction enzyme Sau3AI used to cut the chromosomal DNA, for example, BamHI, is allowed to act on the vector DNA under a condition of a temperature not less than 30° C. and an enzyme concentration of 1 to 100 units/ml for not less than 1 hour, preferably for 1 to 3 hours to completely digest it, and cut and cleave it. Next, the chromosomal DNA fragment mixture obtained as described above is mixed with the cleaved and cut vector DNA, on which DNA ligase, preferably T4 DNA ligase is allowed to act under a condition of a temperature of 4 to 16° C. at an enzyme concentration of 1 to 100 units/ml for not less than 1 hour, preferably for 6 to 24 hours to obtain recombinant DNA.

The obtained recombinant DNA is used to transform a microorganism belonging to the genus Escherichia, for example, a DDPS deficient mutant strain such as an *Escherichia coli* K-12 strain, preferably a JE7627 strain (ponB704 dacB12 pfv$^+$ tonA2 dapA lysA str malA38 metB1 ilvH611 leuA371 proA3 lac-3tsx-76) to prepare a chromosomal DNA library. The transformation can be performed, for example, by a method of D. M. Morrison (*Methods in Enzymology* 68, 326 (1979)) or a method in which recipient bacterial cells are treated with calcium chloride to increase permeability of DNA (Mandel, M. and Higa, A., *J. Mol. Biol.,* 53, 159 (1970)). The JE7627 strain is available from National Institute of Genetics (Mishima-shi, Shizuoka-ken, Japan).

A bacterial strain having recombinant DNA of the DDPS gene is obtained from strains having increased DDPS activity or strains in which auxotrophy resulting from deficiency in DDPS gene is complemented, among the obtained chromosomal DNA library. For example, a DDPS deficient mutant strain requires diaminopimelic acid. Thus when the DDPS deficient mutant strain is used as a host, a DNA fragment containing the DDPS gene can be obtained by isolating a bacterial strain which becomes capable of growing on a medium containing no diaminopimelic acid, and recovering recombinant DNA from the bacterial strain.

Confirmation of the fact whether or not a candidate strain having recombinant DNA containing a DDPS gene actually harbors recombinant DNA in which the DDPS gene is cloned can be achieved by preparing a cellular extract from the candidate strain, and preparing a crude enzyme solution therefrom to confirm whether or not the DDPS activity has been increased. A procedure to measure the enzyme activity of DDPS can be performed by a method of Yugari et al. (Yugari, Y. and Gilvarg, C., *J. Biol. Chem.,* 240, 4710 (1962)).

Recombinant DNA in which DNA containing the DDPS gene is inserted into the vector DNA can be isolated from the bacterial strain described above by means of, for example, a method of P. Guerry et al. (*J. Bacteriol.,* 116, 1064 (1973)) or a method of D. B. Clewell (*J. Bacteriol.,* 110, 667 (1972)).

Preparation of the wild type DDPS gene can be also performed by preparing chromosomal DNA from a strain having a DDPS gene on chromosome by means of a method of Saito and Miura or the like, and amplifying the DDPS gene by means of a polymerase chain reaction (PCR) method (see White, T. J. et al.; *Trends Genet.*, 5, 185 (1989)). DNA primers to be used for the amplification reaction are those complementary to both 3'-terminals of a double stranded DNA containing an entire region or a partial region of the DDPS gene. When only a partial region of the DDPS gene is amplified, it is necessary to use such DNA fragments as primers to perform screening of a DNA fragment containing the entire region from a chromosomal DNA library. When the entire region of the DDPS gene is amplified, a PCR reaction solution including DNA fragments containing the amplified DDPS gene is subjected to agarose gel electrophoresis, and then an aimed DNA fragment is extracted. Thus a DNA fragment containing the DDPS gene can be recovered.

The DNA primers may be adequately prepared on the basis of, for example, a sequence known *E. coli* (Richaud, F. et al., *J. Bacteriol.*, 297 (1986)). Concretely, primers which can amplify a region comprising 1150 bases coding for the DDPS gene are preferable, and two species of primers defined in SEQ ID NO:1 and NO:2 are suitable. Synthesis of the primers can be performed by an ordinary method such as a phosphoamidite method (see *Tetrahedron Letters*, 22, 1859 (1981)) by using a commercially available DNA synthesizer (for example, DNA Synthesizer Model 380B produced by Applied Biosystems). Further, the PCR can be performed by using a commercially available PCR apparatus (for example, DNA Thermal Cycler Model PJ2000 produced by Takara Shuzo Co., Ltd.), using Taq DNA polymerase (supplied by Takara Shuzo Co., Ltd.) in accordance with a method designated by the supplier.

With respect to the DDPS gene amplified by the PCR method, operations such as introduction of mutation into the DDPS gene become easy, when it is ligated with a vector DNA autonomously replicable in cells of bacteria belonging to the genus Escherichia, and introduced into cells of bacteria belonging to the genus Escherichia. The vector DNA to be used, the transformation method, and the confirmation method for the presence of the DDPS gene are the same as those in the aforementioned procedure.

DDPS gene originating from a bacterium belonging to the genus Serratia can be obtained in the same manner as the above, and the gene can be isolated from chromosomal DNA libraries of bacteria belonging to the genus Serratia by hybridization using DDPS gene originating from *E. coli* or a part thereof as a probe. Also, the DDPS gene originating from a bacterium belonging to the genus Serratia can be obtained by PCR method using a chromosommal DNA of a bacterium belonging to the genus Serratia as a template and oligonucleotide prepared based on base sequence of DDPS gene originating from *E. coli*, for example, oligonucleotides having two kinds of sequences as shown in SEQ ID Nos. 1 and 2 as a primer.

Bacteria belonging to the genus Serratia are closely related to bacteria belonging to the genus Escherichia, and it is known that homology of amino acid sequences of proteins and base sequences of genes in cells is high between both of the bacteria. As such gene, for example, there are known thrA, thrB and thrC, each homology of which are 83%, 73% and 84%, respectively (K. Omori et al., J. Bacteriol., 175, 785–794 (1993)). Further, as an instance of isolation of a gene of bacteria belonging to the genus Serratia by using a gene sequence originating from bacteria belonging to the genus Escherichia, dnaA is known (O. Skovgaard and F. G. Hansen, J. Bacteriol., 169, 3976–3981 (1987)). Therefore, it is certain that the DDPS gene of bacteria belonging to the genus Serratia can be isolated by hybridization or PCR method based on a base sequence of a DDPS gene of bacteria belonging to Escherichia.

(2) Introduction of mutation into DDPS gene

The method for carrying out mutation such as replacement, insertion and deletion of amino acid residues is exemplified by a recombinant PCR method (Higuchi, R., 61, in *PCR Technology* (Erlich, H. A. Eds., Stockton press (1989))), and a site-specific mutagenesis method (Kramer, W. and Frits, H. J., *Meth. in Enzymol.*, 154, 350 (1987); Kunkel T. A. et al., *Meth. in Enzymol.*, 154, 367 (1987)). Aimed mutation can be caused at an aimed site by using these methods.

Further, according to chemical synthesis of an aimed gene, it is possible to introduce mutation or random mutation into an aimed site.

Further, a method is available in which the DDPS gene on chromosome or plasmid is directly treated with hydroxylamine (Hashimoto, T. and Sekiguchi, M. *J. Bacteriol.*, 159, 1039 (1984)). Alternatively, it is acceptable to use a method in which a bacterium belonging to the genus Escherichia having the DDPS gene is irradiated by ultraviolet light, or a method based on a treatment with a chemical agent such as N-methyl-N'-nitrosoguanidine or nitrous acid. According to these methods, mutation can be introduced randomly.

With respect to a selection method for the mutant gene, recombinant DNA comprising a DNA fragment containing the DDPS gene and vector DNA is at first directly subjected to a mutation treatment with hydroxylamine or the like, which is used to transform, for example, an *E. coli* W3110 strain. Next, transformed strains are cultivated on a minimal medium such as M9 containing S-2-aminoethylcysteine (AEC) as an analog of L-lysine. Strains harboring recombinant DNA containing the wild type DDPS gene cannot synthesize L-lysine and diaminopimelic acid (DAP) and are suppressed in growth because DDPS expressed from the recombinant DNA is inhibited by AEC. On the contrary, a strain harboring recombinant DNA containing the DDPS gene in which inhibition by L-lysine is desensitized has a mutant enzyme encoded by the DDPS gene in the aforementioned recombinant DNA, which is not inhibited by AEC. Thus it should be capable of growth on the minimal medium in which AEC is added. This phenomenon can be utilized to select a strain which is resistant in growth to AEC as an analog of L-lysine, that is, a strain harboring recombinant DNA containing a mutant DDPS gene in which inhibition is desensitized.

The mutant gene thus obtained may be introduced as a recombinant DNA into a bacterium belonging to the genus Serratia, and expressed. Thus a bacterium can be obtained which harbors DDPS in which feedback inhibition is desensitized. Alternatively, a mutant DDPS gene fragment may be taken out from the recombinant DNA, and inserted into another vector to make use. The vector DNA which can be used in the present invention is preferably plasmid vector DNA, which is exemplified by pUC19, pUC18, pBR322, pHSG299, pHSG298, pHSG399, pHSG398, RSF1010, pMW119, pMW118, pMW219 and pMW218. Besides, vectors of phage DNA can be also utilized.

Further, in order to express the mutant DDPS gene efficiently, another promoter which works in cells of bacteria belonging to the genus Serratia such as lac, trp and PL may be ligated upstream from a DNA sequence coding for the mutant DDPS, or a promoter contained in the DDPS gene may be used as it is, or after amplifying the promoter.

<2> DNA coding for mutant aspartokinase (AK) used for the present invention

The DNA coding for mutant AK used for the present invention has mutation to desensitize feedback inhibition of encoded AK by L-lysine in DNA coding for wild type AK. AK is exemplified by those originating from bacteria belonging to the genus Escherichia, especially AKIII originating from *E. coli*. Further, any aspartokinase of bacteria belonging to the genus Serratia, provided that it has mutation to desensitize feedback inhibition by L-lysine.

The mutation to desensitize feedback inhibition of AKIII by L-lysine is exemplified by:

(a) mutation to replace a 323rd glycine residue with an aspartic acid residue;

(b) mutation to replace the 323rd glycine residue with the aspartic acid residue and replace a 408th glycine residue with an aspartic acid residue;

(c) mutation to replace a 34th arginine residue with a cysteine residue and replace the 323rd glycine residue with the aspartic acid residue;

(d) mutation to replace a 325th leucine residue with a phenylalanine residue;

(e) mutation to replace a 318th methionine residue with an isoleucine residue;

(f) mutation to replace the 318th methionine residue with the isoleucine residue and replace a 349th valine residue with a methionine residue;

(g) mutation to replace a 345th serine residue with a leucine residue;

(h) mutation to replace a 347th valine residue with a methionine residue;

(i) mutation to replace a 352nd threonine residue with an isoleucine residue;

(j) mutation to replace the 352nd threonine residue with the isoleucine residue and replace a 369th serine residue with a phenylalanine residue;

(k) mutation to replace a 164th glutamic acid residue with a lysine residue; and (l) mutation to replace a 417th methionine residue with an isoleucine residue and replace a 419th cysteine residue with a tyrosine residue;

as counted from the N-terminal of AKIII in an amino acid sequence of AKIII defined in SEQ ID NO:8 in Sequence Listing.

As the DNA coding for the wild type AKIII, for example, DNA coding for AKIII originating from a bacterium belonging to the genus Escherichia such as $E.$ $coli$ is mentioned. Concretely, there are exemplified DNA coding for an amino acid sequence defined in SEQ ID NO:8, and a sequence represented by base numbers 584–1930 in a base sequence defined in SEQ ID NO:7. Incidentally, AKIII of $E.$ $coli$ is encoded by a lysC gene.

In these sequences, those which have mutation in base sequence to cause replacement of amino acid residues described above are examples of DNA coding for the mutant AKIII used for the present invention. Any codon corresponding to the replaced amino acid residue is available especially regardless of its kind, provided that it codes for the identical amino acid residue. Further, there are those in which amino acid sequences of possessed wild type AKIII are slightly different depending on difference in bacterial species and bacterial strains. Those having replacement, deletion or insertion of amino acid residue(s) at position(s) irrelevant to enzyme activity in such a manner are also included in the mutant AKIII gene used for the present invention. For example, a base sequence of a wild type lysC gene obtained in Example 2 described below (SEQ ID NO:7) is different from an already published sequence of lysC of an $E.$ $coli$ K-12 JC411 strain at 6 sites (Cassan, M., Parsot, C., Cohen, G. N., and Patte, J. C.,$J.$ $Biol.$ $Chem.,$ 261 1052 (1986)). Encoded amino acid residues are different at 2 sites of them (in lysC of the JC411 strain, a 58th glycine residue is replaced with a cysteine residue, and a 401st glycine residue is replaced with an alanine residue, as counted from the N-terminal in an amino acid sequence of lysC defined in SEQ ID NO:8). It is expected even for lysC having the same sequence as that of lysC of the $E.$ $coli$ K-12 JC411 strain that lysC having mutation in which feedback inhibition by L-lysine is desensitized is obtained if any of the aforementioned mutation of (a) to (l) is introduced.

A method for obtaining DNA coding for the mutant AK in which feedback inhibition by L-lysine is desensitized is as follows. At first, a DNA containing a wild type AK gene or AK gene having another mutation is subjected to an in vitro mutation treatment, and a DNA after the mutation treatment is ligated with a vector DNA adapted to a host to obtain a recombinant DNA. The recombinant DNA is introduced into a host microorganism to obtain transformants. When one which expresses a mutant AK is selected among the aforementioned transformants, such a transformant harbors a mutant gene. Alternatively, a DNA containing a wild type AK gene or AK gene having another mutation may be ligated with a vector DNA adapted to a host to obtain a recombinant DNA. The recombinant DNA is thereafter subjected to an in vitro mutation treatment, and a recombinant DNA after the mutation treatment is introduced into a host microorganism to obtain transformants. When one which expresses a mutant AK is selected among the aforementioned transformants, such a transformant also harbors a mutant gene.

Alternatively, it is also acceptable that a microorganism which produces a wild type enzyme is subjected to a mutation treatment to create a mutant strain whi h produces a mutant enzyme, and then a mutant gene is obtained from the mutant strain. The agent for performing a direct mutation treatment of DNA is exemplified by hydroxylamine and the like. Hydroxylamine is a chemical mutation treatment agent which causes mutation from cytosine to thymine by changing cytosine to $N^4$-hydroxycytosine. Alternatively, when a microorganisms itself is subjected to a mutation treatment, the treatment is performed by ultraviolet light irradiation, or using a mutating agent usually used for artificial mutation such as N-methyl-N'-nitro-N-nitrosoguanidine (NTG).

Any one is used as a donor microorganism for DNA containing the wild type AK gene or AK gene having another mutation described above, provided that it is a microorganism belonging to the genus Escherichia or the genus Serratia. Concretely, it is possible to utilize those described in a book written by Neidhardt et al. (Neidhardt, F. C. et al., $Escherichia$ $coli$ and $Salmonella$ $typhimurium,$ American Society for Microbiology, Washington D.C., 1208, table 1). For example, an $E.$ $coli$ JM109 strain and an MC1061 strain are exemplified. Also, the microorganism belonging to the genus Serratia is exemplified by $Serratia$ $marcescens,$ for example, $Serratia$ $marcescens$ AJ13125 strain (FERM BP-5441).

When the AK gene is obtained from these strains, preparation of chromosomal DNA, preparation of a chromosomal DNA library and the like may be performed in the same manner as the preparation of the DDPS gene described above. As the host to be used for preparation of the library, it is preferable to use a strain entirely deficient in AKI, II and III such as an $E.$ $coli$ GT3 strain (available from $E.$ $coli$ Genetic Stock Center (Connecticut, United States)).

From the obtained chromosomal DNA library, a bacterial strain having a recombinant DNA of the AK gene is obtained as a strain in which the AK activity is increased, or a strain in which auxotrophy is complemente. Cellular extracts are prepared from candidate strains, and crude enzyme solutions are prepared therefrom to confi m the AK activity. The measurement procedure for the AK enzyme activity may be performed in accordance with a method of Stadtman et al. (Stadtman, E. R., Cohen, G. N., LeBras, G., and Robichon-Szulmajster, H., $J.$ $Biol.$ $Chem.,$ 236, 2033 (1961)).

For example, when a mutant strain completely deficient in AK is used as a host, a DNA fragment containing an AK gene can be obtained by isolating a transformed strain which becomes capable of growing on a medium not containing L-lysine, L-threonine, L-methionine and diaminopimelic acid, or on a medium not containing homoserine and diaminopimelic acid, and recovering recombinant DNA from the bacterial strain.

When the AK gene is amplified from chromosomal DNA by means of the PCR method, DNA primers to be used for the PCR reaction can be properly prepared on the basis of, for example, a sequence known in *E. coli* (Cassan, M., Parsot, C., Cohen, G. N., and Patte, J. C., *J. Biol. Chem.*, 261, 1052 (1986)). However, primers which can amplify a region comprising 1347 bases coding for lysC gene is suitable, and for example, two primers having sequences defined in SEQ ID NO:5 and NO:6 are suitable.

Further, AK gene originating from a bacterium belonging to the genus Serratia can be obtained in the same manner as the above, and the gene can be isolated from chromosomal DNA libraries of bacteria belonging to the genus Serratia by hybridization using AK gene originating from *E. coli* or a part thereof as a probe. Also, the AK gene originating from a bacterium belonging to the genus Serratia can be obtained by PCR method using a chromosommal DNA of a bacterium belonging to the genus Serratia as a template and oligonucleotide prepared based on base sequence of AK gene originating from *E. coli*.

The method for carrying out mutation such as replacement, insertion and deletion of amino acid residue(s) on the AK gene obtained as described above is exemplified by the recombinant PCR method, the site specific mutagenesis method and the like, in the same manner as the mutation treatment of the DDPS gene described above.

Further, according to chemical synthesis of an aimed gene, it is possible to introduce mutation or random mutation into an aimed site.

Further, a method is available in which DNA of the AK gene on chromosome or extrachromosomal recombinant DNA is directly treated with hydroxylamine (Hashimoto, T. and Sekiguchi, M. *J. Bacteriol.*, 159, 1039 (1984)). Alternatively, it is acceptable to use a method in which a bacterium belonging to the genus Escherichia having an AK gene on chromosome or extrachromosomal recombinant DNA is irradiated by ultraviolet light, or a method to perform a treatment with a chemical agent such as N-methyl-N'-nitrosoguanidine or nitrous acid.

With respect to a selection method for the mutant AK gene, a strain completely deficient in AK, for example, an *E. coli* GT3 strain is at first transformed with a recombinant DNA containing an AK gene having been subjected to the mutation treatment. Next, transformed strains are cultivated on a minimal medium such as M9 containing a considerable amount of L-lysine. Strains harboring recombinant DNA containing a wild type AK gene cannot synthesize L-threonine, L-isoleucine, L-methionine and diaminopimelic acid (DAP) and are suppressed in growth because only one AK is inhibited by L-lysine. On the contrary, the strain harboring recombinant DNA containing the mutant AK gene in which inhibition by L-lysine is desensitized should be capable of growth on the minimal medium to which the considerable amount of L-lysine is added. This phenomenon can be utilized to select a strain which is resistant in growth to L-lysine or AEC as an analog of L-lysine, that is, a strain harboring recombinant DNA containing a mutant AK gene in which inhibition is desensitized.

The mutant gene thus obtained may be introduced as a recombinant DNA into a bacterium belonging to the genus Serratia, and expressed. Thus the bacterium can be obtained which harbors AK in which feedback inhibition is desensitized. Alternatively, a mutant AK gene fragment may be taken out from the recombinant DNA, and inserted into another vector to make use. The vector DNA which can be used in the present invention is preferably plasmid vector DNA, for which there are exemplified pUC19, pUC18, pBR322, pHSG299, pHSG298, pHSG399, pHSG398, RSF1010, pMW119, pMW118, pMW219 and pMW218. Besides, vectors of phage DNA can be also utilized.

Further, in order to express the mutant AK gene efficiently, another promoter which works in cells of bacteria belonging to the genus Serratia such as lac, trp and PL may be ligated upstream from a DNA sequence coding for the mutant AK, or a promoter contained in the AK gene may be used as it is, or after amplifying it.

<3> Production of L-lysine according to the present invention

L-Lysine can be efficiently produced by cultivating, in an appropriate medium, the bacterium belonging to the genus Serratia transformed by introducing the mutant DDPS gene obtained as described above and allowed to harbor AK in which feedback inhibition by L-lysine is desensitized, producing and accumulating L-lysine in a culture thereof, and collecting L-lysine from the culture. Specifically, L-lysine can be efficiently produced by allowing the bacterium belonging to the genus Serratia to harbor both of the mutant DDPS and the mutant AK.

The bacterium belonging to the genus Serratia harboring AK in which feedback inhibition by L-lysine is desensitized is exemplified by bacteria belonging to the genus Serratia transformed by introducing, into cells, a recombinant DNA constructed by ligating a DNA coding for AK having mutation to desensitize feedback inhibition by L-lysine with a vector DNA autonomously replicable in cells of bacteria belonging to the genus Serratia. Further, AK in which feedback inhibition by L-lysine is desensitized may be a wild type AK which does not suffer feedback inhibition by L-lysine, or one to which such a wild type AK gene is introduced into a bacterium belonging to the genus Serratia in the same manner. Further, a mutant strain of a bacterium belonging to the genus Serratia, which has become to produce a mutant AK by means of a mutation treatment of cells of a bacterium belonging to the genus Serratia, is also acceptable.

On the other hand, in order to achieve transformation by introducing the mutant DDPS gene into a bacterium belonging to the genus Serratia, transformation may be achieved by introducing, into cells, a recombinant DNA constructed by ligating the mutant DDPS gene with a vector DNA autonomously replicable in cells of bacteria belonging to the genus Serratia.

When the both of the mutant DDPS gene and the mutant AK gene are introduced into a bacterium belonging to the genus Serratia, the both mutant genes may be harbored on an identical plasmid or separated plasmids in cells. When separated plasmids are used, it is preferable to use plasmids having a stable distribution mechanism to allow each of them to be stably harbored in the cell. When the mutant DDPS gene and the mutant AK gene are introduced into a bacterium belonging to the genus Serratia by using the separate plasmids, any order of introduction of the both genes is acceptable.

The productivity of L-lysine can be further improved by enhancing a dihydrodipicolinate reductase gene (dapB) of the bacterium belonging to the genus Serratia in which the mutant DDPS gene and the mutant AK gene have been introduced. The productivity of L-lysine can be still further improved by introducing a diaminopimelate dehydrogenase gene (DDH) originating from a Coryne-type bacterium into the bacterium belonging to the genus Serratia which harboring the mutant AK gene and the mutant DDPS gene and in which the dihydrodipicolinate reductase gene has been enhanced. This diaminopimelate dehydrogenase gene should be enhanced. Alternatively, the productivity of L-lysine can be also improved in a similar degree by enhancing a succinyldiaminopimelate transaminase gene (dapD) and a succinyldiaminopimelate deacylase gene (dapE) instead of the introduction of the diaminopimelate dehydrogenase.

The enhancement of gene herein refers to enhancement in activity of an enzyme as an expression product of the gene per cell. Concretely, there may be exemplified enhancement in copy number of the gene in a cell, enhancement in expression amount per gene by using a promoter having a high expression efficiency, and introduction of mutation to enhance enzyme activity into the gene. In order to enhance the copy number of a gene in a cell, the gene is inserted into a vector autonomously replicable in bacteria belonging to the genus Serratia, and a bacterium belonging to the genus Serratia may be transformed with this vector. This vector is preferably a multi-copy type plasmid. Alternatively, the copy number may be increased by amplifying DNA integrated into chromosomal DNA by using Mu phage or the like.

With respect to the use of the plasmid, when plasmids are used for introduction of the mutant DDPS gene and the mutant AK gene, such plasmids having a stable distribution mechanism are preferably used in which these plasmids are stably harbored in a cell together. Any order of introduction of the genes is acceptable.

A method for obtaining the genes of the L-lysine biosynthesis system of *E. coli* coli and the DDH gene of the Coryne-type bacterium will be exemplified below.

The DDH gene is obtained by amplifying chromosomal DNA of the Coryne-type bacterium such as *Brevibacterium lactofermentum* by means of the PCR method by using two species of oligonucleotide primers (for example, SEQ ID NO:9, NO:10) prepared on the basis of a known nucleotide sequence of a DDH gene of *Corynebacterium glutamicum* (Ishino, S. et al., *Nucleic Acids Res.*, 15, 3917 (1987)).

The dapD gene is obtained by amplifying chromosomal DNA of an *E. coli* W3110 strain by means of the PCR method by using two species of oligonucleotide primers (for example, SEQ ID NO:11, NO:12) prepared on the basis of a nucleotide sequence of a known dapD gene (Richaud, C. et al., *J. Biol. Chem.*, 259, 14824 (1984)).

The dapE gene is obtained by amplifying *E. coli* DNA by means of the PCR method by using two species of oligonucleotide primers (SEQ ID NO:13, NO:14) prepared on the basis of a nucleotide sequence of a known dapE gene (Bouvier, J. et al., *J. Bacteriol.*, 174, 5265 (1992)).

In the present invention, any bacterium belonging to the genus Serratia is available for the use as a host provided that a promoter of the mutant DDPS gene, the mutant AK gene or another gene of the L-lysine biosynthesis system, or another promoter for expressing these genes functions in its cells, and a replication origin of a vector DNA to be used for introduction functions in its cells to be capable of replication when the mutant DDPS gene, the mutant AK gene or another gene of the L-lysine biosynthesis system is introduced into a plasmid as extrachromosomal DNA.

For example, a bacterium belonging to the genus Serratia is exemplified by L-threonine-producing microorganisms, because inhibition of their aspartokinase by L-lysine is generally desensitized also in the L-threonine-producing microorganisms. As an L-threonine-producing bacterium belonging to *S. marcescens*, one resistant to AHV (α-amino-β-hydroxyvaleric acid) which is a threonine analog (S. Komatsubara, M. Kisumi and I. Chiba, Appl. Environ. Microbiol., 35, 834 (1978)). As such strain, there is *Seratia marcescens* AJ13125 strain. The strain was deposited in National Institute of Bioscience and Human Technology, Agency of Indastrial Science and Technology (1-3, Higashi 1-chome, Tsukuba-shi, Ibaraki-ken, 305 Japan) under an accession number of FERM P-14983 on Jun. 12, 1995 and trasferred to an international deposition under the Budapest Treaty on Mar. 4, 1996, and an accession number of FERM BP-5441 was assigned.

Further, as a bacterium belonging to the genus Serratia usable in the present invention, *Seratia marcescens* deficient in lysine decarboxylase is exemplified (Japanese Patent Application Laid-Open No. 50-53589 (1975)). Lysine decarboxylase is an enzyme catalyzing a reaction of producing cadaverine by decarboxylation of L-lysine as an L-lysine degrading enzyme, and the strain deficient therein is suppressed in degradation of L-lysine.

L-Threonine-producing bacteria and bacteria belonging to the genus Serratia deficient in lysine decarboxylase may be obtained by ultraviolet irradiation or treatment by mutagens such as N-methyl-N'-nitro-N-nitrosoguanidine and nitric acid, which are ordinarily used for artificial mutation.

The medium to be used for cultivation of the transformant harboring the mutant gene according to the present invention is an ordinary medium containing a carbon source, a nitrogen source, inorganic ions and optionally other organic components.

As the carbon source, it is possible to use sugars such as sucrose, glucose, lactose, galactose, fructose, or starch hydrolysate; alcohols such as glycerol or sorbitol; or organic acids such as fumaric acid, citric acid or succinic acid.

As the nitrogen source, it is possible to use inorganic ammonium salts such as urea, ammonium sulfate, ammonium chloride or ammonium phosphate; organic nitrogen such as soybean hydrolysate; ammonia gas; or aqueous ammonia.

It is preferable to allow required substances such as vitamin $B_1$ and L-isoleucine or yeast extract to be contained in appropriate amounts as organic trace nutrients. Other than the above, potassium phosphate, magnesium sulfate, iron ion, manganese ion and the like are added in small amounts, if necessary.

Cultivation is preferably carried out under an aerobic condition for 16 to 96 hours. The cultivation temperature is controlled at 25° C. to 45° C., and pH is controlled at 5 to 8 during cultivation. Inorganic or organic, acidic or alkaline substances as well as ammonia gas or the like can be used for pH adjustment.

Collection of L-lysine from a fermented liquor is usually carried out by combining an ion exchange resin method, a precipitation method and other known methods.

BRIEF DESCRIPTION OF THE DRAWINGS

FIG. 1 shows preparation steps for pdapA1 and pdapA2.

FIG. 2 shows inhibition by L-lysine for wild type and mutant DDPS's.

FIG. 7 shows preparation steps for a plasmid RSF24P originating from RSF1010 having dapA*24.

BEST MODE FOR CARRYING OUT THE INVENTION

Figure 3:
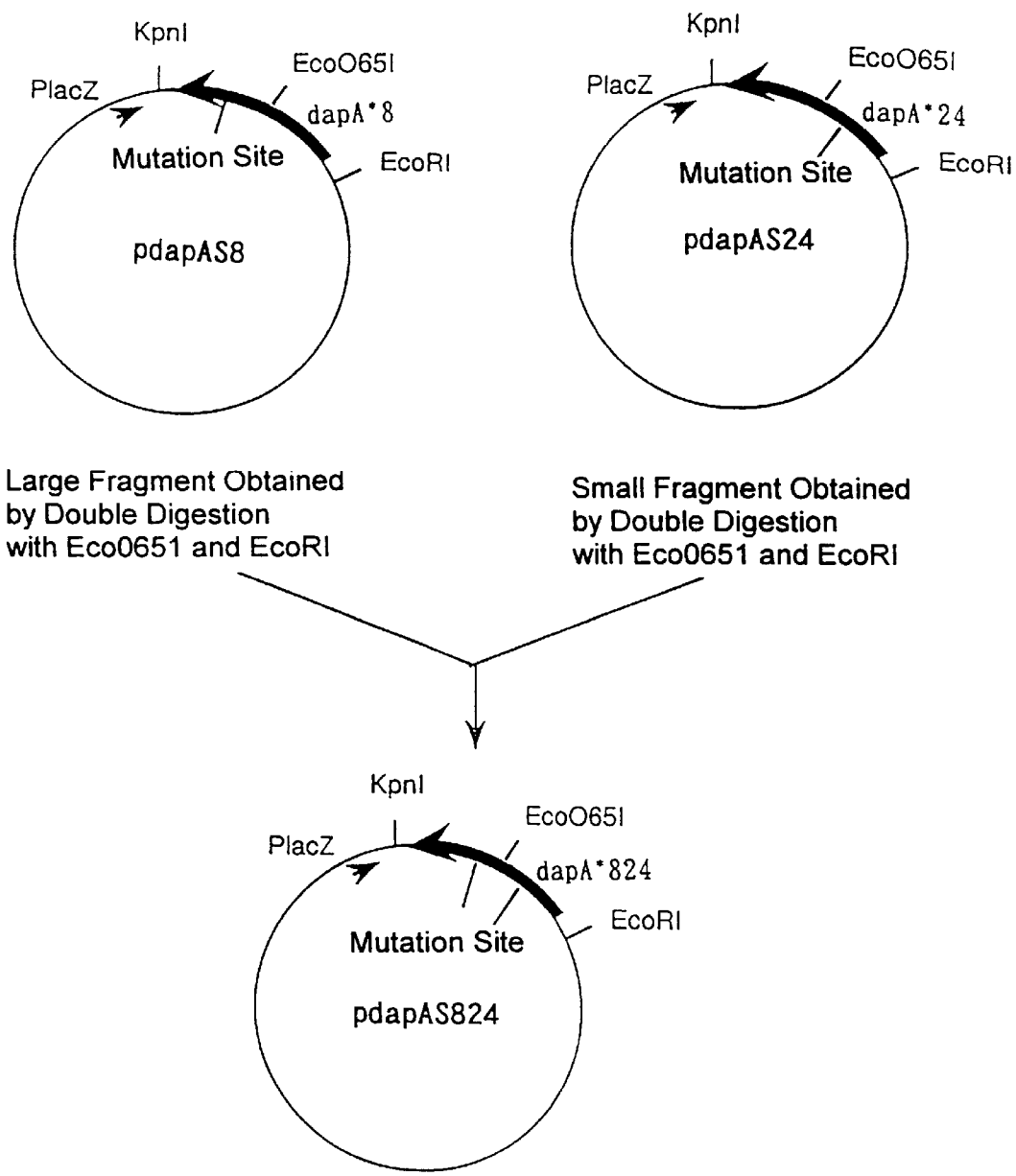
FIG. 3 shows preparation steps for a plasmid pdapAS824 having a double mutation type dapA* gene.

The present invention will be more concretely explained below with reference to Examples.

EXAMPLE 1

Preparation of Mutant DDPS Gene

<1> Cloning of wild type dapA gene

A base sequence of a dapA gene of *E. coli* has been already reported (Richaud, F. et al., *J. Bacteriol.*, 297 (1986)), and it is known that its open reading frame (ORF) has 876 base pairs, and codes for a protein having 292 amino acid residues. Since it is unknown how this dapA gene is regulated, a region containing only an SD sequence and ORF except for a promoter region was amplified by using the PCR method and cloned.

Total genomic DNA of an *E. coli* K-12 MC1061 strain was extracted in accordance with a method of Saito and Miura (*Biochem. Biophys. Acta.*, 72, 619 (1963)). Two species of primers having sequences shown in SEQ ID NO:1 and NO:2 were prepared, which were used to perform the PCR reaction in accordance with a method of Erlich et al. (*PCR Technology*, Stockton press (1989)), and target DNA was amplified. Obtained DNA was inserted into a commercially available cloning vector pCR1000 for PCR fragments (purchased from Invitrogen, Ltd., (California, the United States)) as it was. pCR1000 contains a lacZ promoter (Placz), and is sold in a state of being cut at a site downstream from the lacZ promoter. When a recombinant DNA obtained by ligating a PCR fragment between both cut termini of pCR1000 is introduced into *E. coli*, the PCR fragment is transcribed under control of the lacZ promoter. Upon ligation of the PCR fragment with pCR1000, two species of plasmids were obtained, which were pdapA1 as a plasmid ligated in a positive orientation and pdapA2 as a plasmid ligated in a reversed orientation, for the direction of transcription of dapA with respect to the direction of transcription by the lacZ promoter (FIG. 1).

When these plasmids were introduced into *E. coli* JE7627 which is a strain deficient in DDPS, strains with the introduced plasmids is complemented for auxotrophy for diaminopimelic acid of the host JE7627. Thus it was confirmed that DNA fragments inserted into the both plasmids contain the gene dapA coding for active DDPS.

A transformed strain obtained by introducing pdapA1 into a wild type *E. coli* W3110 strain (available from National Institute of Genetics (Mishima-shi, Shizuoka-ken, Japan)) was designated as W3110/pdapA1, and a transformed strain obtained by introducing pdapA2 into the *E. coli* W3110 strain was designated as W3110/pdapA2, respectively. These two transformed strains were cultivated respectively in a minimal medium M9 having the following composition to which AEC as an analog of lysine was added. The W3110 strain with no introduced plasmid was also cultivated in the same medium as a control. These two transformed strains and the W3110 strain having no plasmid were suppressed in growth by AEC, however, their growth inhibition was recovered by addition of L-lysine.

| | Minimal medium M9 | |
|---|---|---|
| A: | (20 × M9) | |
| | $Na_2HPO_4 \cdot 12H_2O$ | 303 g/L |
| | $KH_2PO_4$ | 60 g/L |
| | NaCl | 10 g/L |
| | $NH_4Cl$ | 20 g/L |
| B: | 1 M $MgSO_4$ | |
| C: | 50% Glucose | |
| D: | 1 g/L Thiamine | |

A, B, C and D described above were separately sterilized, and mixed in a ratio of A:B:C:D:water=5:0.1:1:0.1:95.

<2> Preparation of mutant DDPS gene (dapA*)

It was assumed that a strain harboring a plasmid containing dapA* coding for DDPS with desensitized inhibition by L-lysine could grow on a minimal medium M9 to which a considerable amount of AEC was added. A strain harboring a plamid containing dapA* was selected by their growth resistance to AEC.

In order to efficiently obtain dapA*, dapA*'s on pdapA1 and pdapA2 prepared in <1> were subjected to a mutation treatment.

(1-2-1) Investigation on selection condition for strain harboring plasmid containing dapA*

The W3110/pdapA1 strain and the W3110/pdapA2 strain obtained as described above were cultivated on M9 agar plate media containing various concentrations of AEC, respectively. Growth inhibitory concentrations by AEC were examined, and a selection condition was investigated for a strain harboring a plasmid containing dapA*.

Growth of the transformants on the M9 media containing AEC at various concentrations is shown in Table 1. In this table, + indicates growth of transformant, and – indicates no growth.

TABLE 1

| AEC concentration (mM) | W3110/pdapA1 | W3110/pdapA2 |
|---|---|---|
| 250 | – | – |
| 125 | – | – |
| 60 | – | – |
| 30 | – | – |
| 15 | + | – |
| 8 | + | + |
| 4 | + | + |
| 2 | + | + |

The direction of transcription of the dapA gene on pdapA1 coincides with the direction of transcription by the lacZ promoter (FIG. 1). Thus it was found that the dapA gene on pdapA1 provided resistance to AEC at considerably high concentrations even when dapA remained as a wild type because its expression amount was amplified by the lacZ promoter, while the dapA gene on pdapA2 had a smaller expression amount and provided inhibition in growth by AEC at lower concentrations because the direction of transcription was in the reversed direction with respect to the lacZ promoter, and a promoter of dapA's own was also deficient (the growth was suppressed in an allotment of addition of 30 mM in the case of the W3110/pdapA1 strain, and of 15 mM in the case of the W3110/pdapA2 strain). It was confirmed that the growth inhibition was eliminated by simultaneous addition of L-lysine.

Therefore, pdapA2 was used as an object for introduction of mutation. A medium prepared by adding 60 mM of AEC to the minimal medium M9 was used for selection of a strain harboring a plasmid containing dapA*. This medium is referred to as "selection medium" in Example 1 below.

(1-2-2) In vitro mutation treatment for pdapA2 with hydroxylamine

An in vitro mutation treatment method in which plasmids were directly treated with hydroxylamine was used for introduction of mutation into the pdapA2 plasmid.

2 µg of DNA was treated at 75° C. for 1 to 4 hours in 0.4 M hydroxylamine (0.1 M $KH_2PO_4$-1 MM EDTA (pH 6.0): 100 µl, 1 M hydroxylamine-1 mM EDTA (pH 6.0): 80 µl, DNA: 2 µg, total: 200 µl by filling up with water). DNA after the treatment was purified with glass powder, and introduced into *E. coli* W3110, and it was spread on a complete medium (L-broth: 1% Bacto trypton, 0.5% Yeast extract, 0.5% NaCl, 1.5% agar) to form colonies. They were replicated onto the selection medium described in (1-2-1), and those which formed colonies on the selection medium were selected. Candidates of mutant plasmids in a total of 36 strains were obtained after two times of experiments.

The candidate strains of 36 strains in total thus obtained were spotted on the selection medium again, and AEC resistance was confirmed.

(1-2-3) Isolation of dapA* gene and investigation on dapA* product

Mutant pdapA2's were recovered from the 36 strains described above. A dapA-deficient strain, JE7627 was transformed with them and the wild type pdapA2, respectively. A cell-free extract was prepared from each of the transformed strains, and the enzyme activity of DDPS was measured.

The cell-free extract (crude enzyme solution) was prepared as follows. A transformed strain was cultivated in a 2 x TY medium (1.6% Bacto trypton, 1% Yeast extract, 0.5% NaCl), and collected at an optical density at 660 nm ($OD_{660}$) of about 0.8. A cell pellet was washed with 0.85% NaCl under a condition of 0° C., and suspended in 20 mM potassium phosphate buffer (pH 7.5) containing 400 mM KCl. The cells were disrupted by sonication (0° C., 200 W, 10 minutes). A disrupted cell solution was centrifuged at 33 krpm for 1 hour under a condition of 0° C. to obtain a supernatant to which ammonium sulfate was added to give 80% saturation to be stored at 0° C. overnight followed by centrifugation. A pellet was dissolved in 20 mM potassium phosphate buffer (pH 7.5)-400 mM KCl.

The enzyme activity of DDPS was measured in accordance with a method of Yugari et al. (Yugari, Y. and Gilvarg, C., J. Biol. Chem., 240, 4710 (1962)). Namely, the absorbance of a reaction solution having the following composition was measured at 37° C. with a spectrophotometer at a wavelength of 270 nm in a time-course manner, and generated dihydrodipicolinate was measured. Sodium pyruvate was removed from the reaction system to be used as a blank.

(Composition of reaction solution)
50 mM imidazole-HCl pH 7.4
20 mM L-aspartic semialdehyde
20 mM sodium pyruvate
enzyme solution
water (balance)
total 1.0 ml In measurement of the enzyme activity of DDPS, various concentrations of L-lysine were added to the enzyme reaction solutionand the degree of inhibition by L-lysine was examined. As shown in FIG. 2, the wild type DDPS suffered inhibition by L-lysine. Mutant plasmids originating from the transformed strains having DDPS difficult to suffer inhibition by L-lysine as compared with the wild type were three species among the 36 species of the candidate plasmids. They were designated as pdapAS8, pdapAS9 and pdapAS24, respectively. According to following determination of base sequences, it was revealed that pdapAS8 and pdapAS9 had the same mutation.

The degree of desensitization of inhibition by L-lysine was varied in the three species of mutant DDPS encoded by pdapAS8, pdapAS9 and pdapAS24, however, the inhibition by L-lysine was desensitized in all of the three species. Although the specific activity of the enzyme might be affected by growth situations of cells and preparation of samples, it was found to be lowered a little in any case as compared with the wild type. However, it was judged that no substantial problem would be caused by them as a material for breeding.

(1-2-4) Determination of base sequence of mutant dapA gene

Base sequences of the mutant dapA genes were determined in accordance with an ordinary method by using a DNA sequencer ABI Model 373A (produced by Applied Biosystem Inc.). As a result, it was revealed that 487th C was changed to T in pdapAS8 and pdapAS9, and 597th C was changed to T in pdapAS24 on a sequence of the wild type dapA gene shown in SEQ ID NO:3. Therefore, it was revealed that an 81st alanine residue was changed to a valine residue in DDPS encoded by pdapAS8 and pdapAS9, and a 118th histidine residue was changed to a tyrosine residue in DDPS encoded by pdapAS24 in an amino acid sequence of DDPS shown in SEQ ID NO:4.

(1-2-5) Preparation of dapA having double mutation

Two species of the mutant dapA genes were obtained as described above. In order to verify whether or not desensitization of inhibition works additively for these mutations, a plasmid containing mutant dapA having both of the two mutations was prepared. A procedure of preparation is as shown in FIG. 3. An obtained plasmid having double mutation was designated as pdapAS824.

EXAMPLE 2

Preparation of Mutant AKIII Gene

<1> Cloning of wild type lysC gene

A base sequence of an AKIII gene (lysC) of E. coli has been already reported (Cassan, M., Parsot, C., Cohen, G. N., and Patte, J. C., J. Biol. Chem., 261, 1052 (1986)), and it is known that its open reading frame (ORF) has 1347 base pairs, and codes for a protein having 449 amino acid residues. An operator is present in this gene, and is subjected to suppression by L-lysine. Thus in order to remove the operator region, a region containing only an SD sequence and ORF was amplified by using the PCR method and cloned.

Figure 4:
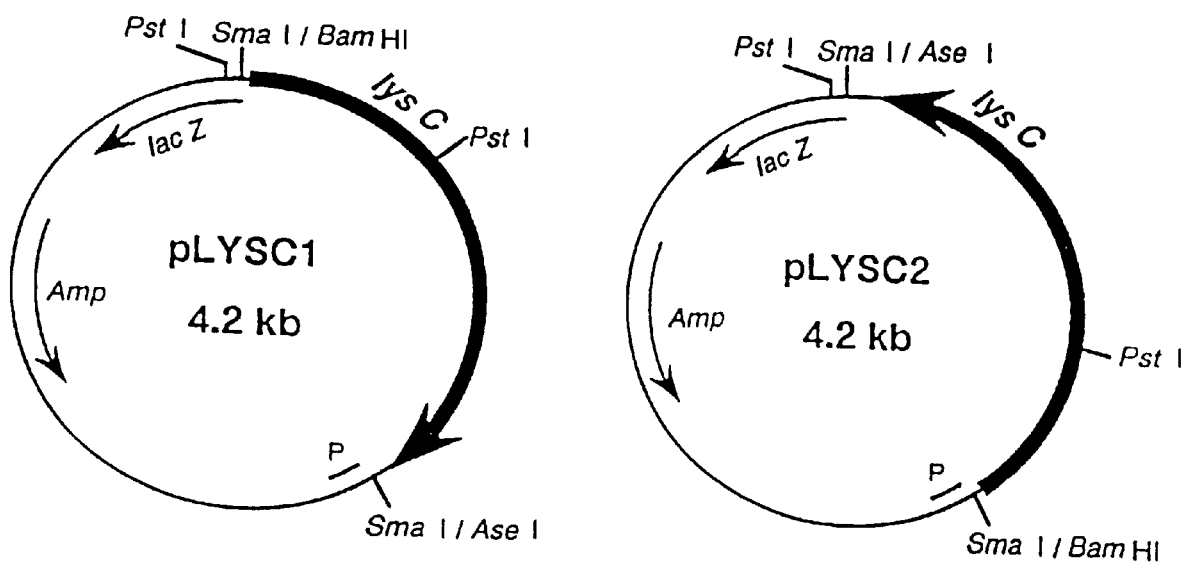
FIG. 4 shows preparation steps for pLYSC1 and pLYSC2.

Total genomic DNA of an E. coli K-12 MC1061 strain was prepared in accordance with a method of Saito and Miura (Biochem. Biophys. Acta., 72, 619 (1963)). Two species of primers having sequences shown in SEQ ID NO:5 and NO:6 were prepared, which were used to perform the PCR reaction in accordance with a method of Erlich et al. (PCR Technology, Stockton press (1989)), and the lysC gene was amplified. Obtained DNA was digested with BamHI and AseI, then blunt-ended, and inserted into a SmaI site of a multi-copy vector, pUC18. This SmaI site is located at a downstream side from a lacZ promoter existing in the vector, and when recombinant DNA obtained by inserting a DNA fragment into the SmaI site of pUC18 is introduced into E. coli, the inserted DNA fragment is transcribed by means of read-through transcription under the control by the lacZ promoter. Upon insertion of the PCR fragment into the SmaI site of pUC18, two species of plasmids were obtained, which were pLYSC1 as a plasmid inserted in a reversed orientation and pLYSC2 as a plasmid inserted in a positive orientation, for the direction of transcription of lysC with respect to the direction of transcription by the lacZ promoter (FIG. 4).

When these plasmids were used to transform E. coli GT3 (thrA1016b metLM1005 lysC1004) as a completely deficient strain for AKI, II, III, auxotrophy of GT3 for homoserine and diaminopimelic acid was complemented. Thus it was confirmed that DNA fragments inserted into the both plasmids contain the gene lysC coding for active AKIII.

A transformed strain obtained by introducing pLYSC1 into the AK completely deficient strain, E. coli GT3 was designated as GT3/pLYSC1, and a transformed strain obtained by introducing pLYSC2 into the E. coli GT3 was designated as GT3/pLYSC2. A considerable amount of L-lysine was added to the minimal medium M9, and the GT3/pLYSC1 strain and the GT3/pLYSC2 strain were each cultivated. Both of the GT3/pLYSC1 strain and the GT3/pLYSC2 strain harbor plasmids containing the wild type lysC, in which AKIII encoded by lysC on the plasmids is a sole AK. The wild type AKIII as the sole AK is inhibited by L-lysine in the presence of a considerable amount of L-lysine. Thus the both strains could not synthesize L-threonine, L-isoleucine, L-methionine and diaminopimelic acid (DAP), and were suppressed in growth.

<2> Preparation of mutant AKIII gene (lysC*)

It was assumed that a strain harboring a plasmid containing lysC* coding for AK with desensitized inhibition by L-lysine could grow on a minimal medium M9 to which a considerable amount of L-lysine was added. A strain harboring a plasmid containing lysC* was selected by selecting strains with their growth resistant to L-lysine or AEC as an analog of L-lysine.

In order to efficiently obtain lysC*, lysC's on pLYSC1 and pLYSC2 prepared in <1> were subjected to a mutation treatment.

(2-2-1) Investigation on selection condition for strain harboring plasmid containing lysC*

The GT3/pLYSC1 strain and the GT3/pLYSC2 strain were cultivated on M9 agar plate media containing various concentrations of L-lysine or AEC, respectively. Growth inhibitory concentrations by L-lysine and AEC were examined, and a selection condition was investigated for a strain harboring a plasmid containing lysC*.

Growth of the transformants on the M9 media containing L-lysine or AEC at various concentrations is shown in Table 2. In this table, + indicates growth of transformant, ± indicates a little growth, and − indicates no growth.

TABLE 2

Growth and L-lysine concentration

| | (mM) | | | | | | | | | | |
|---|---|---|---|---|---|---|---|---|---|---|---|
| | 0 | 0.2 | 0.4 | 0.8 | 1.5 | 3 | 6 | 12 | 25 | 50 | 100 | 200 |
| GT3/pLYSC1 | + | − | − | − | − | − | − | − | − | − | − | − |
| GT3/pLYSC2 | + | + | + | + | + | + | + | + | + | + | ± | − |

Growth and AEC concentration

| | (mM) | | | | | | | | | |
|---|---|---|---|---|---|---|---|---|---|---|
| | 0 | 0.2 | 0.4 | 0.8 | 1.5 | 3 | 6 | 12 | 25 | 50 |
| GT3/pLYSC1 | + | − | − | − | − | − | − | − | − | − |
| GT3/pLYSC2 | + | ± | ± | ± | ± | ± | − | − | − | − |

The direction of transcription of the lysC gene on pLYSC2 coincides with the direction of transcription by the lacZ promoter (FIG. 4). Thus it was found that the lysC gene on pLYSC2 provided resistance to L-lysine and AEC at considerably high concentrations even when lysC remained as a wild type because its expression amount was amplified by the lacZ promoter, while the lysC gene on pLYSC1 had a smaller expression amount and provided inhibition in growth by L-lysine and AEC at lower concentrations because the direction of transcription was in the reversed direction with respect to the lacZ promoter, and a promoter of itself was also deficient (the growth was not suppressed up to an allotment of addition of 100 mM for L-lysine and up to an allotment of addition of 3 mM for AEC in the case of the GT3/pLYSC2 strain, while the growth was completely suppressed in an allotment of addition of 0.2 mM for both L-lysine and AEC in the case of GT3/pLYSC1 strain). It was confirmed that the growth inhibition was eliminated by simultaneous addition of homoserine and diaminopimelic acid.

Therefore, pLYSC1 was used for experiments of introduction of mutation. A medium prepared by adding 10 mM of L-lysine or 0.2 mM of AEC to the minimal medium M9 was used for selection of a strain harboring a plasmid containing lysC*. This medium is referred to as "selection medium" in Example 2 below.

(2-2-2) In vitro mutation treatment for pLYSC1 with hydroxylamine

Two kinds of methods were used for introduction of mutation into the pLYSC1 plasmid, which were an in vitro mutation treatment method in which plasmids are directly treated with hydroxylamine, and an additional in vivo mutation treatment method in which a cell harboring a plasmid is treated with nitrosoguanidine (NTG) followed by extraction of the plasmid in order to provide diversity of mutation, namely expecting mutation other than the mutation from cytosine to thymine with hydroxylamine.

(In vitro mutation treatment with hydroxylamine)

Figure 5:
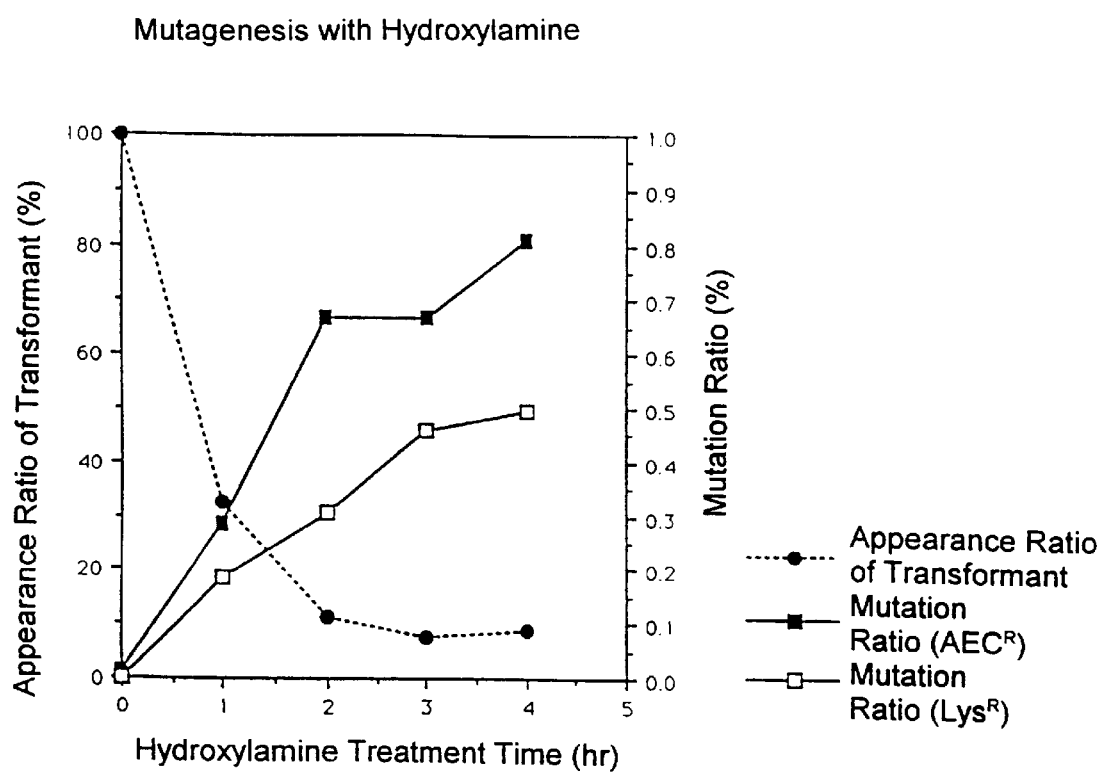
FIG. 5 shows an appearance ratio and a mutation ratio of transformants after a hydroxylamine treatment.

2 μg of DNA was treated under a condition of 75° C. for 1 to 4 hours in 0.4 M hydroxylamine (0.1 M $KH_2PO_4$-1 mM EDTA (pH 6.0): 100 μl, 1 M hydroxylamine-1 mM EDTA (pH 6.0): 80 μl, DNA: 2 μg, total: 200 μl by filling up with water). DNA after the treatment was purified with glass powder, introduced into an AK completely deficient strain, an E. coli GT3 strain, and it was spread on a complete medium (L-broth: 1% Bacto trypton, 0.5% Yeast extract, 0.5% NaCl, 1.5% agar) to form colonies. They were replicated onto the selection medium described in (2-2-1), and strains capable of growth on the selection medium were selected as candidate strains. The appearance ratio of transformants and the mutation ratio were found to change as shown in FIG. 5. Mutant strains were obtained by a treatment for 4 hours at a considerably high ratio of 0.5 to 0.8%.

(In vivo mutation treatment with NTG)

pLYSC1 was introduced into E. coli MC1061, and whole cells were subjected to an NTG treatment. The cells after the treatment were cultivated overnight to fix mutation, and then a plasmid was extracted and introduced into E. coli GT3. Namely, the transformed strain was cultivated in a 2 x TY medium (1.6% Bacto trypton, 1% Yeast extract, 0.5% NaCl), collected at an $OD_{660}$ of about 0.3, washed with a TM buffer described below, then suspended in an NTG solution (prepared by dissolving NTG at a concentration of 0.2 mg/ml in TM buffer), and treated at 37° C. for 0 to 90 minutes. The cells were washed with TM buffer and 2 x TY medium, and then mutation was fixed by cultivation in 2 x TY medium overnight. Subsequently plasmid DNA was extracted from the cells, and introduced into an E. coli GT3 strain. Screening of candidate strains was performed in the same manner as in the in vitro mutation, and mutants of lysine resistance ($Lys^R$) and AEC resistance ($AEC^R$) were obtained.

| TM buffer | |
|---|---|
| Tris | 50 mM |
| Maleic acid | 50 mM |
| $(NH_4)_2SO_4$ | 1 g/L |
| $MgSO_4.7H_2O$ | 0.1 g/L |
| $Ca(NO_3)_2$ | 5 mg/L |
| $FeSO_4.7H_2O$ | 0.25 mg/L | pH was adjusted to 6.0 with NaOH.

Total 180 strains of candidate strains obtained as described above (hydroxylamine treatment: 48 strains, NTG treatment: 132 strains) were spotted on the selection medium again, and AEC and L-lysine resistances were confirmed to obtain 153 strains. Taking a notice of difference in amino acid accumulation pattern in the medium, these 153 strains were divided into 14 groups, and the AK activity was measured after selecting representative strains of each of the groups. There was no large difference in AK activity between the mutant strains obtained by the hydroxylamine treatment and the mutant strains obtained by the NTG treatment. Thus the following experiments were performed without distinguishing them.

(2-2-3) Isolation of lysC* gene and investigation on lysC* product

No. 24, No. 43, No. 48, No. 60, No. 80, No. 117, No. 126, No. 149, No. 150, No. 156, No. 158, No. 167, No. 169 and No. 172 were selected as representative strains of the aforementioned 14 groups. Mutant plasmids derived from pLYSC1 were recovered from each of them, and designated as pLYSC1*24, pLYSC1*43, pLYSC1*48, pLYSC1*60, pLYSC1*80, pLYSC1*117, pLYSC1*126, pLYSC1*149, pLYSC1*150, pLYSC1*156, pLYSC1*158, pLYSC1*167, pLYSC1*169 and pLYSC1*172, respectively. An AK completely deficient strain GT3 was transformed with them and the wild type pLYSC1. A cell-free extract was prepared from each of transformed strains, and the enzyme activity of AKIII was measured.

The cell-free extract (crude enzyme solution) was prepared as follows. A transformed strain was cultivated in a 2 x TY medium, and collected at an $OD_{660}$ of about 0.8. Cells were washed with 0.02 M $KH_2PO_4$ (pH 6.75)-0.03 M β-mercaptoethanol under a condition of 0° C., and the cells were disrupted by sonication (0° C., 100 W, 30 minutes×4). A disrupted cell solution was centrifuged at 33 krpm for 1 hour under a condition of 0° C. to obtain a supernatant to which ammonium sulfate was added to give 80% saturation. After centrifugation, a pellet was dissolved in 0.02 M $KH_2PO_4$ (pH 6.75)-0.03 M β-mercaptoethanol, and stored at 0° C. overnight.

The enzyme activity of AKIII was measured in accordance with a method of Stadtman et al. (Stadtman, E. R., Cohen, G. N., LeBras, G., and Robichon-Szulmajster, H., *J. Biol. Chem.*, 236, 2033 (1961)). Namely, a reaction solution having the following composition was incubated at 27° C. for 45 minutes, and an $FeCl_3$ solution (2.8 N HCl 0.4 ml+12% TCA 0.4 ml+5% $FeCl_3 \cdot 6H_2O$/0.1 N HCl 0.7 ml) was added thereto to develop a color, and it was centrifuged followed by measurement of absorbance of a supernatant at 540 nm. The activity was indicated by an amount of hydroxamic acid generated per minute (1 U=1 μmol/min). The molar absorption coefficient was 600. Potassium aspartate was removed from the reaction solution to be used as a blank.

| Composition of reaction solution | |
|---|---|
| reaction mixture *1 | 0.3 ml |
| hydroxylamine solution *2 | 0.2 ml |
| 0.1 M potassium aspartate (pH 7.0) enzyme solution | 0.1 ml |
| water | (balance) |
| total | 1.0 ml |

*1: M Tris-HCl (pH 8.1) 9 ml + 0.3 M $MgSO_4$ 0.5 ml + 0.2 M ATP (pH 7.0) 5 ml
*2: 8 M hydroxylamine solution neutralized just before use with KOH.

Figure 6A:
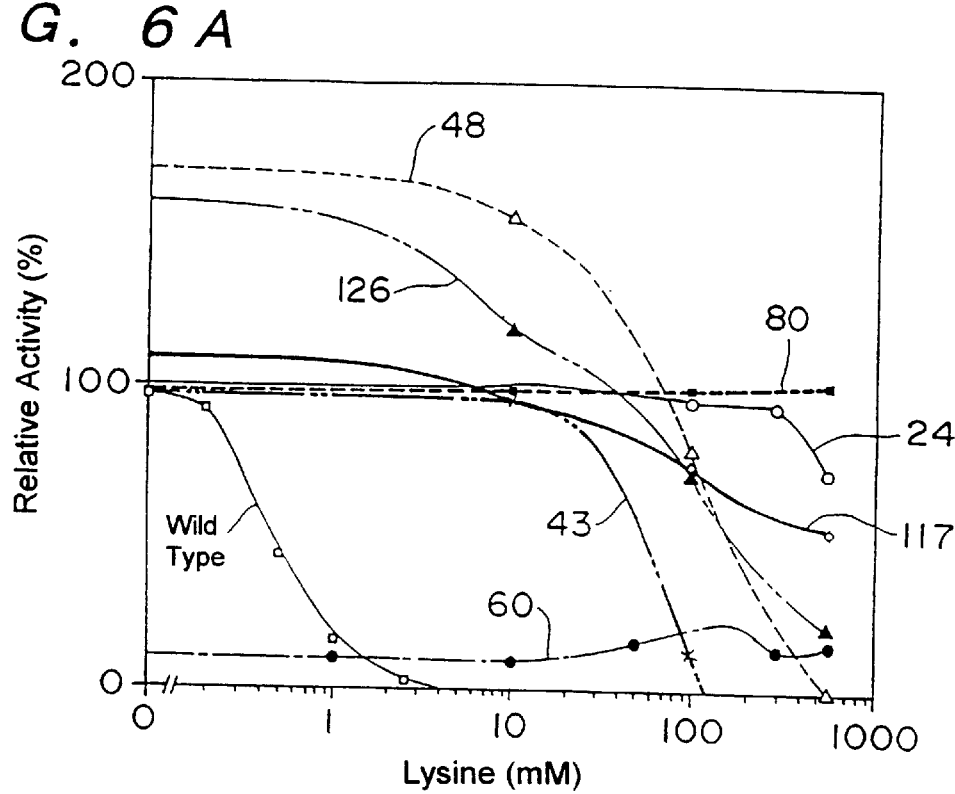
FIGS. 6a and 6b show inhibition by L-lysine for wild type and mutant AKIII's.
Figure 6B:
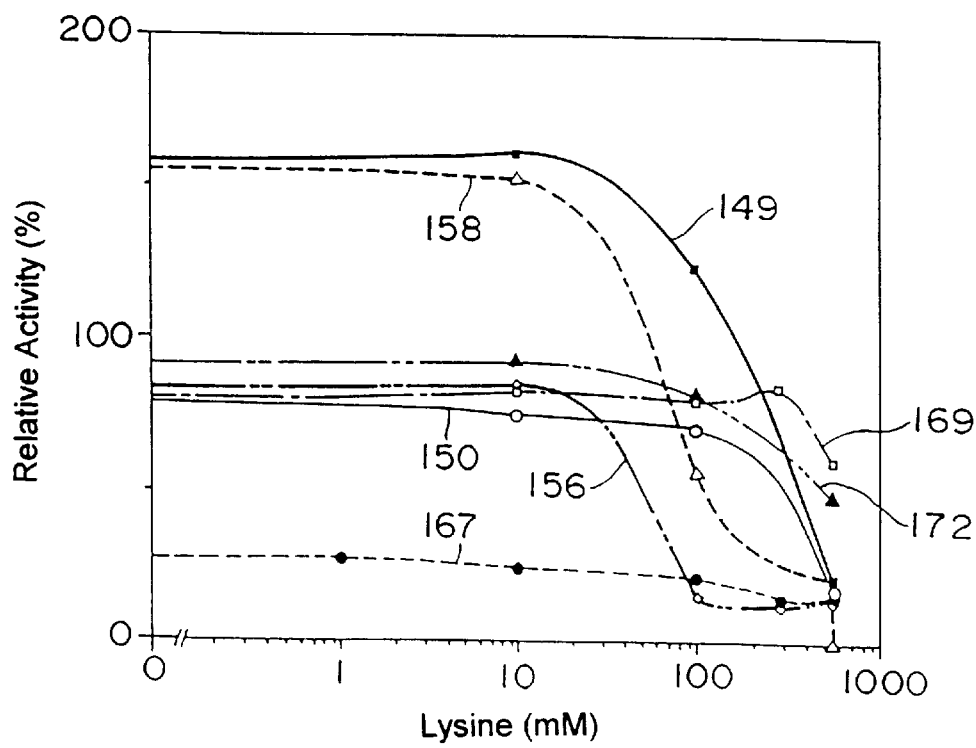

In measurement of the enzyme activity of AK, various concentrations of L-lysine were added to the enzyme reaction solution and the degree of inhibition by L-lysine was examined. Results are shown in FIG. 6 and Table 3. The wild type and Nos. 24, 43, 48, 60, 80, 117 and 126 are shown in FIG. 6A. Nos. 149, 150, 156, 158, 167, 169 and 172 are shown in FIG. 6B.

As shown in these results, the wild type AKIII strongly suffered inhibition by L-lysine, which was inhibited by 50% at about 0.45 mM of L-lysine, and inhibited by about 100% at 5 mM. On the contrary, although the mutant AKIII's obtained this time had various degrees of desensitization, inhibition by L-lysine was desensitized in all of 14 species. Especially in the case of Nos. 24, 80, 117, 169 and 172, inhibition was scarcely observed even at 100 mM of L-lysine, and they had 50%-inhibitory-concentrations which were not less than 200 times as compared with that of the wild type. The specific activity based on total protein, which might be affected by growth situations of cell and preparation of samples, was equal to or more than that of the wild type in almost all cases, and there was little problem of decrease in activity due to the introduction of mutation (Table 3). According to this fact, it was expected that an active center of AKIII was independent from a regulatory site by L-lysine with each other. In Table 3, the inhibition desensitization degree (%) refers to an AK activity in the presence of 100 mM of L-lysine compared with an AK activity in the absence of L-lysine in the reaction solution. The heat stability (%) refers to a ratio of activity maintenance after a treatment at 55° C. for 1.5 hour.

TABLE 3

| | Specific activity (U/mg protein) | Degree of desensitization of inhibition (%)[*1] | Heat stability (%)[*2] |
|---|---|---|---|
| Wild type | 0.0247 | 0 | 18 |
| No. 117 | 0.0069 | 120 | 0 |
| No. 24 | 0.0218 | 100 | 30 |
| No. 80 | 0.0244 | 99 | 36 |
| No. 172 | 0.0189 | 97 | 0 |
| No. 169 | 0.0128 | 96 | 2 |
| No. 150 | 0.0062 | 77 | 25 |
| No. 126 | 0.0250 | 61 | 39 |
| No. 149 | 0.0256 | 59 | 9 |
| No. 167 | 0.0083 | 43 | 45 |
| No. 48 | 0.0228 | 38 | 42 |
| No. 60 | 0.0144 | 35 | 9 |
| No. 158 | 0.0224 | 22 | 42 |
| No. 156 | 0.0101 | 18 | 2 |
| No. 43 | 0.0212 | 17 | 0 |

[*1]: AK activity (%) in the presence of 100 mM of L-lysine compared with AK activity in the absence of L-lysine
[*2]: ratio of activity maintenance (%) after treatment at 55° C. for 1.5 hour Subsequently, the heat stability of the mutant enzymes was examined. When it is intended that an enzyme is improved to increase its activity, it is important that a created enzyme is maintained stably in cells. Measurement in vitro has some problems because of the difference between intracellular and extracellular protease activities and the influence of buffers for in vitro storage of enzymes. However, for convenience, the heat stability of the mutant AKIII's was investigated in vitro as one parameter.

Judging from results of investigation on the inactivation temperature of AKIII under various conditions, the ratio of activity maintenance after a treatment at 55° C. for 90 minutes was measured. As shown in Table 3, half the enzymes were rather more excellent than the wild type. Generally, a mutant enzyme is often unstable as compared with a wild type. However, some of the mutant AKIII's obtained this time were superior to the wild type in stability, and many of them seemed to be fairly useful in practical use for L-lysine production.

(2-2-4) Determination of base sequence of wild type lysC and mutant lysC

A base sequence of the wild type lysC gene obtained this time was determined in accordance with an ordinary method by using a DNA sequencer ABI Model 373A (produced by Applied Biosystem Inc.) (SEQ ID NO:7). As a result, differences were found in six sites (two at the amino acid level) from an already published sequence of lysC of an *E. coli* K-12 JC411 strain (Cassan, M., Rarsot, C., Cohen, G. N., and Patte, J. C., *J. Biol. Chem.*, 261, 1052 (1986)). It is speculated that the difference in six sites is due to the difference in bacterial strain used.

In the same manner, base sequences were determined for each of lysC*'s existing on the 14 species of mutant pLYSC1's, and mutation points were determined. Results are shown in Table 4. In this table, indications in parentheses show mutations of amino acid residues based on mutations of nucleotides. Types of mutations were 12 kinds because two sets (No. 48 and No. 167, No. 24 and No. 80) had exactly the same mutation types among the 14 species. With respect to mutation types, Nos. 149, 150, 156, 158, 167, 169 and 172 were obtained by the hydroxylamine treatment, and Nos. 24, 43, 48, 60, 80, 117 and 126 were obtained by the NTG treatment. However, as for the pattern of mutation, any of them resided in mutation from cytosine to thymine, or mutation from guanine to adenine on a coding strand due to mutation from cytosine to thymine on a noncoding strand.

TABLE 4

Determination of mutation points of lysC*

| lysC* mutation type | Mutagen | Mutation point (amino acid change) |
|---|---|---|
| No. 126 | N | GGT→GA*T ($^{323}$Gly→Asp) |
| No. 43 | N | GGT→GA*T ($^{323}$Gly→Asp) |
|  |  | GGC→GA*C ($^{408}$Gly→Asp) |
| No. 149 | H | CGT→T*GT ($^{34}$Arg→Cys) |
|  |  | GGT→GA*T ($^{323}$Gly→Asp) |
| No. 48/167 | N/H | CTC→T*TC ($^{325}$Leu→Phe) |
| No. 150 | H | ATG→ATA* ($^{318}$Met→Ile) |
| No. 172 | H | $^{775}$C→T (silent) |
|  |  | ATG→ATA* ($^{318}$Met→Ile) |
|  |  | GTG→A*TG ($^{349}$Val→Met) |
| No. 117 | N | TCA→TT*A ($^{345}$Ser→Leu) |
| No. 158 | H | GTG→A*TG ($^{347}$Val→Met) |
| No. 24/80 | N/N | ACC→AT*C ($^{352}$Thr→Ile) |
| No. 169 | H | $^{923}$C→T (silent) |
|  |  | ACC→AT*C ($^{352}$Thr→Ile) |
|  |  | TCT→TT*T ($^{369}$Ser→Phe) |
| No. 60 | N | $^{859}$G→A (silent) |
|  |  | GAA→A*AA ($^{164}$Glu→Lys) |
| No. 156 | H | ATG→ATA* ($^{417}$Met→Ile) |
|  |  | TGT→TA*T ($^{419}$Cys→Tyr) |
|  |  | $^{2014}$C-T (silent) |

*: H; hydroxylamine treatment, N; NTG treatment

EXAMPLE 3

Fermentation Production of L-Lysine with Strain to which dapA* is Introduced

In order to produce L-lysine by using a bacterium belonging to the genus Escherichia, as indicated in Japanese Patent Laid-open No. 56-18596, U.S. Pat. No. 4,346,170 and *Applied Microbiology and Biotechnology*, 15, 227–231 (1982), it is considered to be essential that a host to be enhanced in DDPS has an aspartokinase which is changed not to suffer inhibition by L-lysine. A bacterium belonging to the genus Serratia is predicted to be similar to the bacterium belonging to the genus Escherichia. L-threonine-producing bacteria may be exemplified as such a strain. As for L-threonine-producing *S. marcescens*, a strain resistant to AHV (α-amino-β-hydroxy valeric acid) as a threonine analog is known (S. Komatsubara, M. Kisumi and I. Chiba, Appl. Environ. Microbiol., 35, 834 (1978)). Specifically, as such strain, Serratia marcescens AJ13125 strain is mentioned. The strain was deposited in National Institute of Bioscience and Human Technology, Agency of Indastrial Science and Technology (1-3, Higashi 1-chome, Tsukuba-shi, Ibaraki-ken, 305 Japan) under an accession number of FERM P-14983 on Jun. 12, 1995, and trasferred to an international deposition under the Budapest Treaty on Mar. 4, 1996 and an accession number of FERM BP-5441 was assigned.

On the other hand, dapA* contained in pdapAS24 (in which the 118th histidine residue replaced with a tyrosine residue) was selected as dapA* to be introduced into *S. marcescens*, judging from the degree of desensitization of inhibition and the specific activity of the enzyme. At first, in order to increase the expression amount of dapA* and increase stability of the plasmid, mutant dapA* having existed on pdapAS24 (hereinafter referred to as "dapA*24") was ligated at the downstream from a promoter of a tetracycline resistance gene of pVIC40, and RSF24P was obtained as shown in FIG. 7.

A strain obtained by introducing the plasmid RSF24P into an *E. coli* JM109 strain was designated as AJ12395, which was deposited in National Institute of Bioscience and Human Technology, Agency of Industrial Science and Technology on Oct. 28, 1993, under accession number of FERM P-13935, and transferred from the original deposition to international deposition based on the Budapest Treaty on Nov. 1, 1994, and has been deposited under accession number of FERM BP-4858. Strains harboring pdapAS8 and pdapAS9 were not deposited. However, all of the mutation points of dapA* on each of the plasmids have been determined as described above. Thus it is easy for those skilled in the art to recover the plasmid from the aforementioned deposited bacterium by using a method of Maniatis et al. (Sambrook, J., Fritsch, E. F., Maniatis, T., *Molecular Cloning*, Cold Spring Harbor Laboratory Press, 1.21 (1989)), and to obtain a target gene by using a site-directed mutagenesis method (Sambrook, J., Fritsch, E. F., Maniatis, T., *Molecular Cloning*, Cold Spring Harbor Laboratory Press, 15.63 (1989)).

The plasmid RSF24P was introduced into the AJ13125 strain in accordance with an ordinary method, and AJ13125/RSF24P was obtained. The L-lysine productivity of AJ13125/RSF24P was evaluated.

On the other hand, RSFP was constructed as a control plasmid. Namely, a large fragment was selected from digest of pVIC40 double-degested with BamHI and DraI as shown in FIG. 7, and it was blunt-ended with DNA polymerase Klenow fragment. The blunt-ended large fragment was self-ligated to obtain the plasmid RSFP. RSFP was introduced into the AJ13125 strain in accordance with an ordinary method, and AJ13125/RSFP was obtained. The L-lysine productivity was also evaluated for AJ13125/RSFP.

The cultivation was performed at an agitation of 114 to 116 rpm under a condition of a cultivation period of 72 hours and a temperature of 30° C. by using the following medium. Results are shown in Table 5.

| medium for L-lysine production | | |
|---|---|---|
| A: | $(NH_4)_2SO_4$ | 16 g/L |
|  | $KH_2PO_4$ | 1 g/L |
|  | $MgSO_4.7H_2O$ | 1 g/L |
|  | $FeSO_4.7H_2O$ | 0.01 g/L |
|  | $MnSO_4.5H_2O$ | 0.01 g/L |
|  | Yeast Ext. (Difco) | 2 g/L |
|  | L-methionine | 0.5 g/L |
|  | L-threonine | 0.1 g/L |
|  | L-isoleucine | 0.05 g/L |
|  | pH is adjusted to 7.0 with KOH to be autoclaved at 115° C. for 10 minutes. | (16/20 volume) |
| B: | 20% Glucose (autoclave at 115° C. for 10 minutes) | (4/20 volume) |
| C: | Pharmacopoeial $CaCo_3$ (heat-sterilized in dry state at 180° C. for 2 days) | (30 g/L) |

A and B are mixed in the ratio of A:B = 4:1, C is added to the mixture in an amount of 30 g per liter and dissolved, and an antibiotic (streptomycin: 200 μg/ml) is added.

B: 20% Glucose (autoclave at 115° C. for 10 minutes) (4/20 volume)

C: Pharmacopoeial CaCO$_3$ (heat-sterilized in dry state at 180° C. for 2 days) (30 g/L)

A and B are mixed in the ratio of A:B=4:1, C is added to the mixture in an amount of 30 g per liter and dissolved, and an antibiotic (streptomycin: 200 µg/ml) is added.

TABLE 5

| Bacterial strain | Production amount of L-lysine hydrochloride |
|---|---|
| AJ13125/RSF24P | 3.5 g/L |
| AJ13125/RSFP | 0 g/L |

EXAMPLE 4

Figure 8:
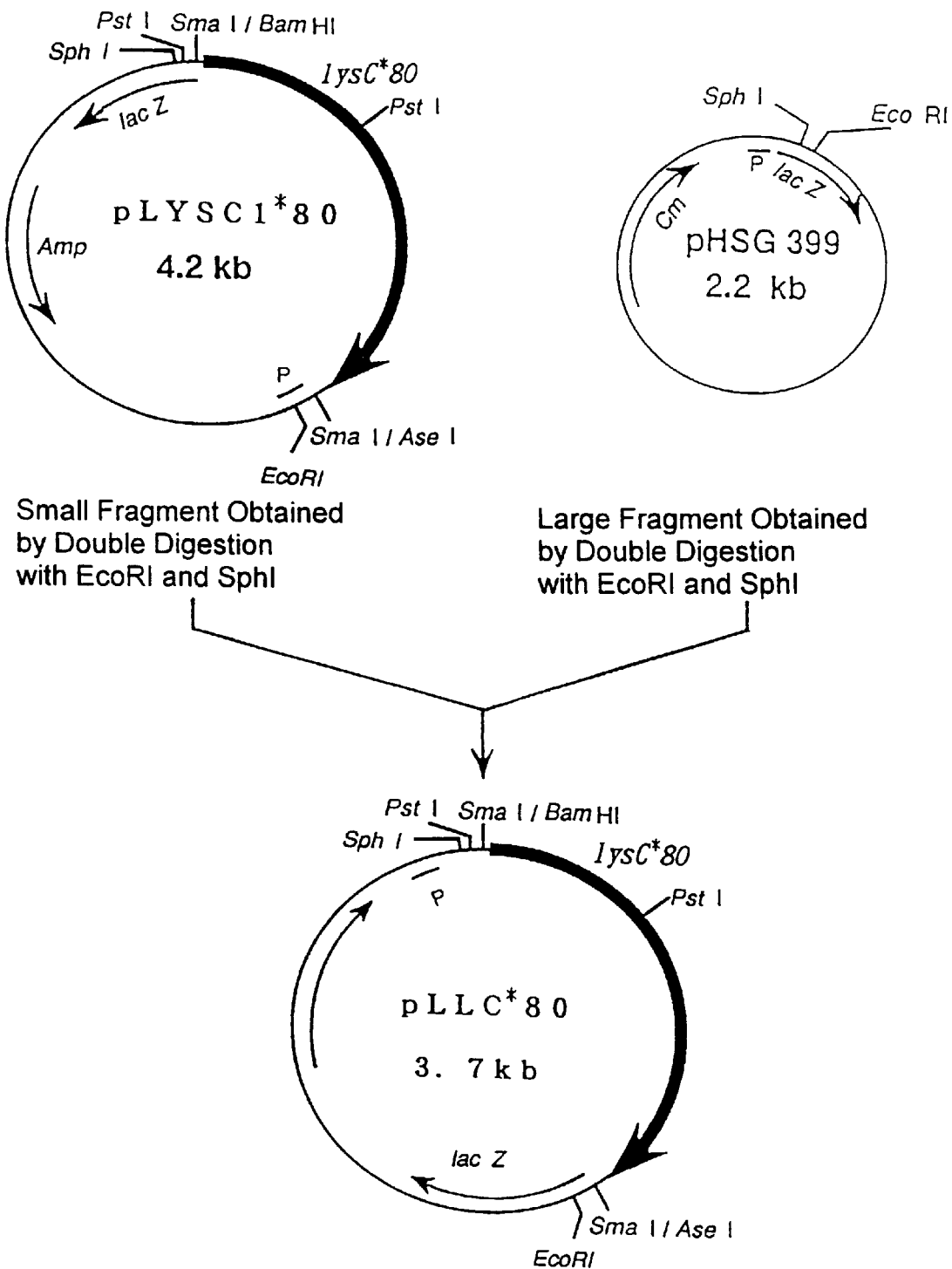
FIG. 8 shows preparation steps for a plasmid pLLC*80.

Fermentation Production of L-Lysine with Strain to which dapA* and lysC* are Introduced The effect of the mutant DDPS on L-lysine production has been shown in Example 3. In order to achieve further improvement, the mutant AKIII gene obtained in Example 2 was allowed to co-exist with the mutant DDPS gene. As the mutant AKIII gene to co-exist with the mutant DDPS gene was selected one originating from the No. 80 strain (lysC*80), judging from the enzyme activity, heat stability and the like.

lysC*80 was used after excising it from a plasmid pLLC*80 (FIG. 8) prepared by ligating lysC* having existed on pLYSC1*80 (hereinafter referred to as "lysC*80") at the downstream of a lacZ promoter of vector pHSG399 (produced by Takara Shuzo Co., Ltd.) which has an inverted-directional-insertion site with respect to pUC18 in order to increase the expression amount of lysC*. pLLC*80 is a plasmid prepared to arrange lysC*80 to allow the direction of transcription to have a positive orientation with respect to the lacZ promoter in order to improve the productivity of L-lysine because lysC*80 on pLYSC1*80 has its direction of transcription arranged in a reversed orientation with respect to the lacZ promoter.

Figure 9:
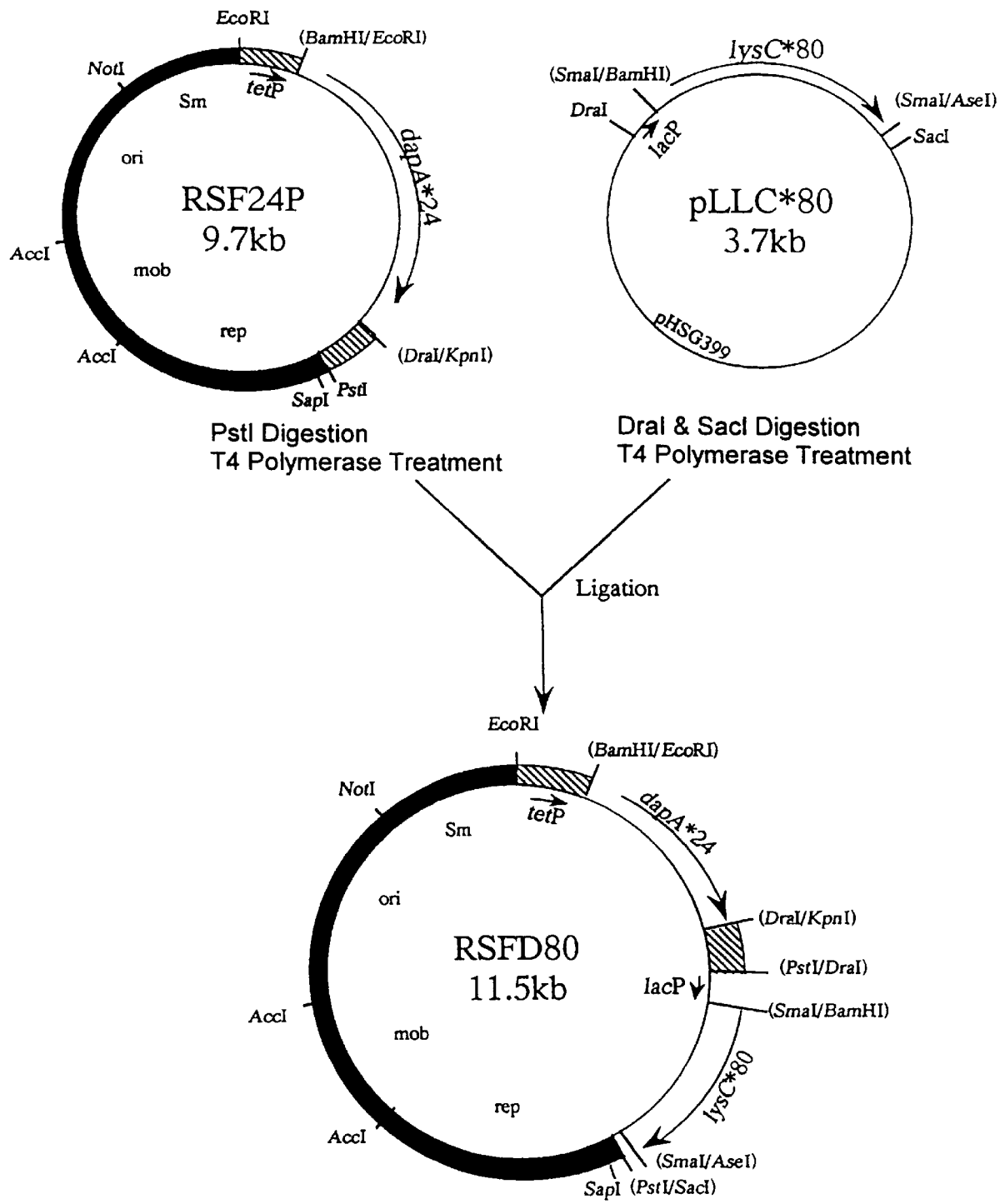
FIG. 9 shows preparation steps for a plasmid RSFD80 originating from RSF1010 having dapA*24 and lysC*80.

A plasmid, RSFD80, having dapA* and lysC* was prepared from pLLC*80 and RSF24P obtained in Example 3 as shown in FIG. 9. RSFD80 includes dapA*24 and lysC*80 arranged in this order to allow the direction of transcription to have a positive orientation with respect to a promoter (tetP) of a tetracycline resistance gene at the downstream from tetP.

The RSFD80 plasmid was introduced into an *E. coli* JM109 strain, which was designated as AJ12396. AJ12396 is deposited in National Institute of Bioscience and Human Technology, Agency of Industrial Science and Technology on Oct. 28, 1993, under accession number FERM P-13936, and transferred from the original deposition to international deposition based on the Budapest Treaty on Nov. 1, 1994, and has been deposited under accession number of FERM BP-4859. Strains harboring pLYSC1*24, pLYSC1*43, pLYSC1*48, pLYSC1*60, pLYSC1*117, pLYSC1*126, pLYSC1*149, pLYSC1*150, pLYSC1*156, pLYSC1*158, pLYSC1*167, pLYSC1*169 and pLYSC1*172 were not deposited. However, all of the mutation points of lysC* on each of the plasmids have been determined as described above. Thus it is easy for those skilled in the art to recover the plasmid from the aforementioned deposited bacterium by using a method of Maniatis et al. (Sambrook, J., Fritsch, E. F., Maniatis, T., *Molecular Cloning,* Cold Spring Harbor Laboratory Press, 1.21 (1989)), and to obtain a target gene by using a site-directed mutagenesis method (Sambrook, J., Fritsch, E. F., Maniatis, T., *Molecular Cloning,* Cold Spring Harbor Laboratory Press, 15.63 (1989)). RSFD80 was introduced into AJ13125 strain in accordance with an ordinary method, and AJ13125/RSFD80 was obtained. The L-lysine productivity of AJ13125/RSFD80 was evaluated. The L-lysine productivity was also evaluated for AJ13125/RSFP as a control.

The cultivation was performed at an agitation of 114 to 116 rpm under a condition of a cultivation period of 72 hours and a temperature of 30° C. by using the same medium for production of L-lysine as in Example 3. Results are shown in Table 6.

TABLE 6

| Bacterial strain | Production amount of L-lysine hydrochloride |
|---|---|
| AJ13125/RSFD80 | 9.2 g/L |
| AJ13125/RSFP | 0 g/L |

INDUSTRIAL APPLICABILITY

According to the present invention, there has been obtained a DDPS mutant gene originating from a bacterium belonging to the genus Escherichia in which feedback inhibition by L-lysine is sufficiently desensitized. A bacterium belonging to the genus Seratia, harboring the gene produces L-lysine in a considerable amount. L-Lysins production can be improved by introducing the mutant DDPS gene into a bacterium belonging to the genus Serratia harboring an aspartokinase in which feedback inhibition by L-lysine is desensitized.

What is claimed is:

1. A bacterium belonging to the genus Serratia comprising a recombinant DNA molecule encoding a mutant Escherichia dihydrodipicolinate synthase that is resistant to L-lysine feedback inhibition, wherein said recombinant DNA molecule encoding said mutant Escherichia dihydrodipicolinate synthase is obtainable by a process comprising subjecting a DNA molecule encoding a wild-type Escherichia dihydrodipicolinate synthase to random mutagenesis and screening for a mutant Escherichia dihydrodipicolinate synthase that is resistant to L-lysine feedback inhibition, and wherein said mutant Escherichia dihydrodipicolinate synthase maintains from about 50% to about 80% of its dihydrodipicolinate synthase activity in the presence of 10 mM L-lysine as it does in the absence of L-lysine.

2. A bacterium belonging to the genus Serratia according to claim 1, wherein the mutation to desensitize feedback inhibition by L-lysine is selected from the group consisting of:
   (1) mutation to replace the alanine residue at the 81st position from the N-terminal of SEQ ID NO:4 with a valine residue,
   (2) mutation to replace the histidine residue at the 118th position from the N-terminal of SEQ ID NO:4 with a tyrosine residue, and
   (3) mutation to replace the alanine residue at the 81st position from the N-terminal of SEQ ID NO:4 with a valine residue and replace the histidine residue at the 118th position from the N-terminal of SEQ ID NO:4 with a tyrosine residue.

3. A bacterium belonging to the genus Serratia according to claim 2, further harboring an aspartokinase in which feedback inhibition by L-lysine is desensitized.

4. A bacterium belonging to the genus Serratia according to claim 3, harboring the aspartokinase in which feedback inhibition by L-lysine is desensitized, as obtained by introducing into its cells, a DNA coding for an aspartokinase having mutation to desensitize feedback inhibition by L-lysine.

5. A bacterium belonging to the genus Serratia according to claim 4, wherein the aspartokinase is an aspartokinase III which is native to a bacterium belonging to the genus Escherichia.

6. A bacterium belonging to the genus Serratia according to claim 5, wherein the mutation to desensitize feedback inhibition of the aspartokinase III by L-lysine is selected from the group consisting of
   (1) mutation to replace the glycine residue at the 323rd position from the N-terminal of SEQ ID NO:8 with an aspartic acid residue,
   (2) mutation to replace the glycine residue at the 323rd position from the N-terminal of SEQ ID NO:8 with an aspartic acid residue and replace the glycine residue at the 408th position from the N-terminal of SEQ ID NO:8 with an aspartic acid residue,
   (3) mutation to replace the arginine residue at the 34th position from the N-terminal of SEQ ID NO:8 with a cysteine residue and replace the glycine residue at the 323rd position from the N-terminal of SEQ ID NO:8 with an aspartic acid residue,
   (4) mutation to replace the leucine residue at the 325th position from the N-terminal of SEQ ID NO:8 with a phenylalanine residue,
   (5) mutation to replace the methionine residue at the 318th position from the N-terminal of SEQ ID NO:8 with an isoleucine residue,
   (6) mutation to replace the methionine residue at the 318th position from the N-terminal of SEQ ID NO:8 with an isoleucine residue and replace the valine residue at the 349th position from the N-terminal of SEQ ID NO:8 with a methionine residue,
   (7) mutation to replace the serine residue at the 345th position from the N-terminal of SEQ ID NO:8 with a leucine residue,
   (8) mutation to replace the valine residue at the 347th position from the N-terminal of SEQ ID NO:8 with a methionine residue,
   (9) mutation to replace the threonine residue at the 352nd position from the N-terminal of SEQ ID NO:8 with an isoleucine residue,
   (10) mutation to replace the threonine residue at the 352nd position from the N-terminal of SEQ ID NO:8 with an isoleucine residue and replace the serine residue at the 369th from the N-terminal of SEQ ID NO:8 with a phenylalanine residue,
   (11) mutation to replace the glutamic acid residue at the 164th position from the N-terminal of SEQ ID NO:8 with a lysine residue, and
   (12) mutation to replace the methionine residue at the 417th position from the N-terminal of SEQ ID NO:8 with an isoleucine residue and replace the cysteine residue at the 419th with a tyrosine residue.

7. A bacterium belonging to the genus Serratia according to claim 1, which is deficient in lysine decarboxylase.

8. A method of producing L-lysine, comprising:
   cultivating the bacterium belonging to the genus Serratia as defined in claim 1 in an appropriate medium, to produce and accumulate L-lysine in the culture thereof, and collecting L-lysine from the culture.

9. A method of producing L-lysine, comprising:
   cultivating the bacterium belonging to the genus Serratia as defined in claim 2 in an appropriate medium, producing and accumulating L-lysine in the culture thereof, and collecting L-lysine from the culture.

10. A method of producing L-lysine, comprising:
    cultivating the bacterium belonging to the genus Serratia as defined in claim 3 in an appropriate medium, producing and accumulating L-lysine in the culture thereof, and collecting L-lysine from the culture.

11. A method of producing L-lysine, comprising:
    cultivating the bacterium belonging to the genus Serratia as defined in claim 4 in an appropriate medium, producing and accumulating L-lysine in the culture thereof, and collecting L-lysine from the culture.

12. A method of producing L-lysine, comprising:
    cultivating the bacterium belonging to the genus Serratia as defined in claim 5 in an appropriate medium, producing and accumulating L-lysine in the culture thereof, and collecting L-lysine from the culture.

13. A method of producing L-lysine, comprising:
    cultivating the bacterium belonging to the genus Serratia as defined in claim 6 in an appropriate medium, producing and accumulating L-lysine in the culture thereof, and collecting L-lysine from the culture.

14. A method of producing L-lysine, comprising:
    cultivating the bacterium belonging to the genus Serratia as defined in claim 7 in an appropriate medium, producing and accumulating L-lysine in the culture thereof, and collecting L-lysine from the culture.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 20
      (B) TYPE: nucleic acid
      (C) STRANDEDNESS: single
      (D) TOPOLOGY: linear

```
       (ii) MOLECULAR TYPE: other..synthetic DNA (xi) SEQUENCE DESCRIPTION: SEQ ID NO:1:

CCGCAACTAC TGACATGACG                                              20

(2) INFORMATION FOR SEQ ID NO:2:

(i) SEQUENCE CHARACTERISTICS:
           (A) LENGTH: 20
           (B) TYPE: nucleic acid
           (C) STRANDEDNESS: single
           (D) TOPOLOGY: linear (ii) MOLECULAR TYPE: other..synthetic DNA (xi) SEQUENCE DESCRIPTION: SEQ ID NO:2:

AGTAAGCCAT CAAATCTCCC                                              20

(2) INFORMATION FOR SEQ ID NO:3:

(i) SEQUENCE CHARACTERISTICS:
           (A) LENGTH: 1197
           (B) TYPE: nucleic acid
           (C) STRANDEDNESS: double
           (D) TOPOLOGY: linear (ii) MOLECULAR TYPE: genomic DNA (vi) ORIGINAL SOURCE:
           (A) ORGANISM: Escherichia coli
           (B) STRAIN: MC1061

(ix) FEATURE:
           (A) NAME/KEY: prim trascript
           (B) LOCATION: 248
           (C) IDENTIFICATION METHOD: E (ix) FEATURE:
           (A) NAME/KEY: CDS
           (B) LOCATION: 272..1150
           (C) IDENTIFICATION METHOD: E (ix) FEATURE:
           (A) NAME/KEY: primer bind
           (B) LOCATION: 27..46
           (C) IDENTIFICATION METHOD: E (ix) FEATURE:
           (A) NAME/KEY: primer bind
           (B) LOCATION: 1156..1175
           (C) IDENTIFICATION METHOD: E (ix) FEATURE:
           (A) NAME/KEY: RBS
           (B) LOCATION: 261..265
           (C) IDENTIFICATION METHOD: S (xi) SEQUENCE DESCRIPTION: SEQ ID NO:3:

CCAGGCGACT GTCTTCAATA TTACAGCCGC AACTACTGAC ATGACGGGTG ATGGTGTTCA    60

CAATTCCACG GCGATCGGCA CCCAACGCAG TGATCACCAG ATAATGTGTT GCGATGACAG   120

TGTCAAACTG GTTATTCCTT TAAGGGGTGA GTTGTTCTTA AGGAAAGCAT AAAAAAAACA   180

TGCATACAAC AATCAGAACG GTTCTGTCTG CTTGCTTTTA ATGCCATACC AAACGTACCA   240

TTGAGACACT TGTTTGCACA GAGGATGGCC C ATG TTC ACG GGA AGT ATT GTC     292
                                  Met Phe Thr Gly Ser Ile Val
                                   1               5

GCG ATT GTT ACT CCG ATG GAT GAA AAA GGT AAT GTC TGT CGG GCT AGC    340
Ala Ile Val Thr Pro Met Asp Glu Lys Gly Asn Val Cys Arg Ala Ser
     10              15                  20

TTG AAA AAA CTG ATT GAT TAT CAT GTC GCC AGC GGT ACT TCG GCG ATC    388
```

```
                Leu Lys Lys Leu Ile Asp Tyr His Val Ala Ser Gly Thr Ser Ala Ile
                    25                  30                  35

GTT TCT GTT GGC ACC ACT GGC GAG TCC GCT ACC TTA AAT CAT GAC GAA              436
Val Ser Val Gly Thr Thr Gly Glu Ser Ala Thr Leu Asn His Asp Glu
40                  45                  50                  55

CAT GCT GAT GTG GTG ATG ATG ACG CTG GAT CTG GCT GAT GGG CGC ATT              484
His Ala Asp Val Val Met Met Thr Leu Asp Leu Ala Asp Gly Arg Ile
                60                  65                  70

CCG GTA ATT GCC GGG ACC GGC GCT AAC GCT ACT GCG GAA GCC ATT AGC              532
Pro Val Ile Ala Gly Thr Gly Ala Asn Ala Thr Ala Glu Ala Ile Ser
            75                  80                  85

CTG ACG CAG CGC TTC AAT GAC AGT GGT ATC GTC GGC TGC CTG ACG GTA              580
Leu Thr Gln Arg Phe Asn Asp Ser Gly Ile Val Gly Cys Leu Thr Val
        90                  95                 100

ACC CCT TAC TAC AAT CGT CCG TCG CAA GAA GGT TTG TAT CAG CAT TTC              628
Thr Pro Tyr Tyr Asn Arg Pro Ser Gln Glu Gly Leu Tyr Gln His Phe
    105                 110                 115

AAA GCC ATC GCT GAG CAT ACT GAC CTG CCG CAA ATT CTG TAT AAT GTG              676
Lys Ala Ile Ala Glu His Thr Asp Leu Pro Gln Ile Leu Tyr Asn Val
120                 125                 130                 135

CCG TCC CGT ACT GGC TGC GAT CTG CTC CCG GAA ACG GTG GGC CGT CTG              724
Pro Ser Arg Thr Gly Cys Asp Leu Leu Pro Glu Thr Val Gly Arg Leu
                140                 145                 150

GCG AAA GTA AAA AAT ATT ATC GGA ATC AAA GAG GCA ACA GGG AAC TTA              772
Ala Lys Val Lys Asn Ile Ile Gly Ile Lys Glu Ala Thr Gly Asn Leu
            155                 160                 165

ACG CGT GTA AAC CAG ATC AAA GAG CTG GTT TCA GAT GAT TTT GTT CTG              820
Thr Arg Val Asn Gln Ile Lys Glu Leu Val Ser Asp Asp Phe Val Leu
        170                 175                 180

CTG AGC GGC GAT GAT GCG AGC GCG CTG GAC TTC ATG CAA TTG GGC GGT              868
Leu Ser Gly Asp Asp Ala Ser Ala Leu Asp Phe Met Gln Leu Gly Gly
    185                 190                 195

CAT GGG GTT ATT TCC GTT ACG ACT AAC GTC GCA GCG CGT GAT ATG GCC              916
His Gly Val Ile Ser Val Thr Thr Asn Val Ala Ala Arg Asp Met Ala
200                 205                 210                 215

CAG ATG TGC AAA CTG GCA GCA GAA GAA CAT TTT GCC GAG GCA CGC GTT              964
Gln Met Cys Lys Leu Ala Ala Glu Glu His Phe Ala Glu Ala Arg Val
                220                 225                 230

ATT AAT CAG CGT CTG ATG CCA TTA CAC AAC AAA CTA TTT GTC GAA CCC             1012
Ile Asn Gln Arg Leu Met Pro Leu His Asn Lys Leu Phe Val Glu Pro
            235                 240                 245

AAT CCA ATC CCG GTG AAA TGG GCA TGT AAG GAA CTG GGT CTT GTG GCG             1060
Asn Pro Ile Pro Val Lys Trp Ala Cys Lys Glu Leu Gly Leu Val Ala
        250                 255                 260

ACC GAT ACG CTG CGC CTG CCA ATG ACA CCA ATC ACC GAC AGT GGT CGT             1108
Thr Asp Thr Leu Arg Leu Pro Met Thr Pro Ile Thr Asp Ser Gly Arg
    265                 270                 275

GAG ACG GTC AGA GCG GCG CTT AAG CAT GCC GGT TTG CTG T AAAGTTTAGG            1158
Glu Thr Val Arg Ala Ala Leu Lys His Ala Gly Leu Leu
280                 285                 290

GAGATTTGAT GGCTTACTCT GTTCAAAAGT CGCGCCTGG                                  1197

(2) INFORMATION FOR SEQ ID NO:4:

(i) SEQUENCE CHARACTERISTICS:
        (A) LENGTH: 292
        (B) TYPE: amino acid
        (D) TOPOLOGY: linear (ii) MOLECULAR TYPE: peptide (xi) SEQUENCE DESCRIPTION: SEQ ID NO:4:
```

```
Met Phe Thr Gly Ser Ile Val Ala Ile Val Thr Pro Met Asp Glu Lys
 1               5                  10                  15

Gly Asn Val Cys Arg Ala Ser Leu Lys Lys Leu Ile Asp Tyr His Val
             20                  25                  30

Ala Ser Gly Thr Ser Ala Ile Val Ser Val Gly Thr Thr Gly Glu Ser
         35                  40                  45

Ala Thr Leu Asn His Asp Glu His Ala Asp Val Val Met Met Thr Leu
     50                  55                  60

Asp Leu Ala Asp Gly Arg Ile Pro Val Ile Ala Gly Thr Gly Ala Asn
 65                  70                  75                  80

Ala Thr Ala Glu Ala Ile Ser Leu Thr Gln Arg Phe Asn Asp Ser Gly
             85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
            115                 120                 125

Pro Gln Ile Leu Tyr Asn Val Pro Ser Arg Thr Gly Cys Asp Leu Leu
130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Thr Asn
            195                 200                 205

Val Ala Ala Arg Asp Met Ala Gln Met Cys Lys Leu Ala Ala Glu Glu
            210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
            275                 280                 285

Ala Gly Leu Leu
            290

(2) INFORMATION FOR SEQ ID NO:5:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULAR TYPE: other..synthetic DNA (xi) SEQUENCE DESCRIPTION: SEQ ID NO:5:

CTTCCCTTGT GCCAAGGCTG                                           20

(2) INFORMATION FOR SEQ ID NO:6:

(i) SEQUENCE CHARACTERISTICS:
        (A) LENGTH: 18
        (B) TYPE: nucleic acid
        (C) STRANDEDNESS: single
```

(D) TOPOLOGY: linear (ii) MOLECULAR TYPE: other..synthetic DNA (xi) SEQUENCE DESCRIPTION: SEQ ID NO:6:

GAATTCCTTT GCGAGCAG                                                    18

(2) INFORMATION FOR SEQ ID NO:7:

(i) SEQUENCE CHARACTERISTICS:
            (A) LENGTH: 2147
            (B) TYPE: nucleic acid
            (C) STRANDEDNESS: double
            (D) TOPOLOGY: linear (ii) MOLECULAR TYPE: genomic DNA (vi) ORIGINAL SOURCE:
            (A) ORGANISM: Escherichia coli
            (B) STRAIN: MC1061

(ix) FEATURE:
            (A) NAME/KEY: -35 signal
            (B) LOCATION: 242..249
            (C) IDENTIFICATION METHOD: S (ix) FEATURE:
            (A) NAME/KEY: -10 signal
            (B) LOCATION: 265..273
            (C) IDENTIFICATION METHOD: S (ix) FEATURE:
            (A) NAME/KEY: primer bind
            (B) LOCATION: 536..555
            (C) IDENTIFICATION METHOD: E (ix) FEATURE:
            (A) NAME/KEY: primer bind
            (B) LOCATION: 2128..2147
            (C) IDENTIFICATION METHOD: E (ix) FEATURE:
            (A) NAME/KEY: RBS
            (B) LOCATION: 575..578
            (C) IDENTIFICATION METHOD: S (ix) FEATURE:
            (A) NAME/KEY: CDS
            (B) LOCATION: 584..1933
            (C) IDENTIFICATION METHOD: S (ix) FEATURE:
            (A) NAME/KEY: terminator
            (B) LOCATION: 1941..1968
            (C) IDENTIFICATION METHOD: S (xi) SEQUENCE DESCRIPTION: SEQ ID NO:7:

TCGAAGTGTT TCTGTAGTGC CTGCCAGGCA GCGGTCTGCG TTGGATTGAT GTTTTTCATT        60

AGCAATACTC TTCTGATTTT GAGAATTGTG ACTTTGGAAG ATTGTAGCGC CAGTCACAGA       120

AAAATGTGAT GGTTTTAGTG CCGTTAGCGT AATGTTGAGT GTAAACCCTT AGCGCAGTGA       180

AGCATTTATT AGCTGAACTA CTGACCGCCA GGAGTGGATG AAAAATCCGC ATGACCCCAT       240

CGTTGACAAC CGCCCCGCTC ACCCTTTATT TATAAATGTA CTACCTGCGC TAGCGCAGGC       300

CAGAAGAGGC GCGTTGCCCA AGTAACGGTG TTGGAGGAGC CAGTCCTGTG ATAACACCTG       360

AGGGGGTGCA TCGCCGAGGT GATTGAACGG CTGGCCACGT TCATCATCGG CTAAGGGGGC       420

TGAATCCCCT GGGTTGTCAC CAGAAGCGTT CGCAGTCGGG CGTTTCGCAA GTGGTGGAGC       480

ACTTCTGGGT GAAAATAGTA GCGAAGTATC GCTCTGCGCC CACCCGTCTT CCGCTCTTCC       540

CTTGTGCCAA GGCTGAAAAT GGATCCCCTG ACACGAGGTA GTT ATG TCT GAA ATT         595
                                                 Met Ser Glu Ile

-continued

1

| | | | | | | | | | | | | | | |
|---|---|---|---|---|---|---|---|---|---|---|---|---|---|---|
| GTT | GTC | TCC | AAA | TTT | GGC | GGT | ACC | AGC | GTA | GCT | GAT | TTT | GAC | GCC | ATG | 643
| Val | Val | Ser | Lys | Phe | Gly | Gly | Thr | Ser | Val | Ala | Asp | Phe | Asp | Ala | Met |
| 5 | | | | 10 | | | | | 15 | | | | | 20 | |

```
GTT GTC TCC AAA TTT GGC GGT ACC AGC GTA GCT GAT TTT GAC GCC ATG        643
Val Val Ser Lys Phe Gly Gly Thr Ser Val Ala Asp Phe Asp Ala Met
 5           10                  15                  20

AAC CGC AGC GCT GAT ATT GTG CTT TCT GAT GCC AAC GTG CGT TTA GTT        691
Asn Arg Ser Ala Asp Ile Val Leu Ser Asp Ala Asn Val Arg Leu Val
             25                  30                  35

GTC CTC TCG GCT TCT GCT GGT ATC ACT AAT CTG CTG GTC GCT TTA GCT        739
Val Leu Ser Ala Ser Ala Gly Ile Thr Asn Leu Leu Val Ala Leu Ala
                 40                  45                  50

GAA GGA CTG GAA CCT GGC GAG CGA TTC GAA AAA CTC GAC GCT ATC CGC        787
Glu Gly Leu Glu Pro Gly Glu Arg Phe Glu Lys Leu Asp Ala Ile Arg
             55                  60                  65

AAC ATC CAG TTT GCC ATT CTG GAA CGT CTG CGT TAC CCG AAC GTT ATC        835
Asn Ile Gln Phe Ala Ile Leu Glu Arg Leu Arg Tyr Pro Asn Val Ile
     70                  75                  80

CGT GAA GAG ATT GAA CGT CTG CTG GAG AAC ATT ACT GTT CTG GCA GAA        883
Arg Glu Glu Ile Glu Arg Leu Leu Glu Asn Ile Thr Val Leu Ala Glu
 85                  90                  95                 100

GCG GCG GCG CTG GCA ACG TCT CCG GCG CTG ACA GAT GAG CTG GTC AGC        931
Ala Ala Ala Leu Ala Thr Ser Pro Ala Leu Thr Asp Glu Leu Val Ser
                105                 110                 115

CAC GGC GAG CTG ATG TCG ACC CTG CTG TTT GTT GAG ATC CTG CGC GAA        979
His Gly Glu Leu Met Ser Thr Leu Leu Phe Val Glu Ile Leu Arg Glu
            120                 125                 130

CGC GAT GTT CAG GCA CAG TGG TTT GAT GTA CGT AAA GTG ATG CGT ACC       1027
Arg Asp Val Gln Ala Gln Trp Phe Asp Val Arg Lys Val Met Arg Thr
            135                 140                 145

AAC GAC CGA TTT GGT CGT GCA GAG CCA GAT ATA GCC GCG CTG GCG GAA       1075
Asn Asp Arg Phe Gly Arg Ala Glu Pro Asp Ile Ala Ala Leu Ala Glu
        150                 155                 160

CTG GCC GCG CTG CAG CTG CTC CCA CGT CTC AAT GAA GGC TTA GTG ATC       1123
Leu Ala Ala Leu Gln Leu Leu Pro Arg Leu Asn Glu Gly Leu Val Ile
165                 170                 175                 180

ACC CAG GGA TTT ATC GGT AGC GAA AAT AAA GGT CGT ACA ACG ACG CTT       1171
Thr Gln Gly Phe Ile Gly Ser Glu Asn Lys Gly Arg Thr Thr Thr Leu
                185                 190                 195

GGC CGT GGA GGC AGC GAT TAT ACG GCA GCC TTG CTG GCG GAG GCT TTA       1219
Gly Arg Gly Gly Ser Asp Tyr Thr Ala Ala Leu Leu Ala Glu Ala Leu
            200                 205                 210

CAC GCA TCT CGT GTT GAT ATC TGG ACC GAC GTC CCG GGC ATC TAC ACC       1267
His Ala Ser Arg Val Asp Ile Trp Thr Asp Val Pro Gly Ile Tyr Thr
            215                 220                 225

ACC GAT CCA CGC GTA GTT TCC GCA GCA AAA CGC ATT GAT GAA ATC GCG       1315
Thr Asp Pro Arg Val Val Ser Ala Ala Lys Arg Ile Asp Glu Ile Ala
        230                 235                 240

TTT GCC GAA GCG GCA GAG ATG GCA ACT TTT GGT GCA AAA GTA CTG CAT       1363
Phe Ala Glu Ala Ala Glu Met Ala Thr Phe Gly Ala Lys Val Leu His
245                 250                 255                 260

CCG GCA ACG TTG CTA CCC GCA GTA CGC AGC GAT ATC CCG GTC TTT GTC       1411
Pro Ala Thr Leu Leu Pro Ala Val Arg Ser Asp Ile Pro Val Phe Val
                265                 270                 275

GGC TCC AGC AAA GAC CCA CGC GCA GGT GGT ACG CTG GTG TGC AAT AAA       1459
Gly Ser Ser Lys Asp Pro Arg Ala Gly Gly Thr Leu Val Cys Asn Lys
            280                 285                 290

ACT GAA AAT CCG CCG CTG TTC CGC GCT CTG GCG CTT CGT CGC AAT CAG       1507
Thr Glu Asn Pro Pro Leu Phe Arg Ala Leu Ala Leu Arg Arg Asn Gln
            295                 300                 305

ACT CTG CTC ACT TTG CAC AGC CTG AAT ATG CTG CAT TCT CGC GGT TTC       1555
Thr Leu Leu Thr Leu His Ser Leu Asn Met Leu His Ser Arg Gly Phe
```

```
            310                 315                 320
CTC GCG GAA GTT TTC GGC ATC CTC GCG CGG CAT AAT ATT TCG GTA GAC    1603
Leu Ala Glu Val Phe Gly Ile Leu Ala Arg His Asn Ile Ser Val Asp
325                 330                 335                 340

TTA ATC ACC ACG TCA GAA GTG AGC GTG GCA TTA ACC CTT GAT ACC ACC    1651
Leu Ile Thr Thr Ser Glu Val Ser Val Ala Leu Thr Leu Asp Thr Thr
                345                 350                 355

GGT TCA ACC TCC ACT GGC GAT ACG TTG CTG ACG CAA TCT CTG CTG ATG    1699
Gly Ser Thr Ser Thr Gly Asp Thr Leu Leu Thr Gln Ser Leu Leu Met
            360                 365                 370

GAG CTT TCC GCA CTG TGT CGG GTG GAG GTG GAA GAA GGT CTG GCG CTG    1747
Glu Leu Ser Ala Leu Cys Arg Val Glu Val Glu Glu Gly Leu Ala Leu
        375                 380                 385

GTC GCG TTG ATT GGC AAT GAC CTG TCA AAA GCC TGC GGC GTT GGC AAA    1795
Val Ala Leu Ile Gly Asn Asp Leu Ser Lys Ala Cys Gly Val Gly Lys
    390                 395                 400

GAG GTA TTC GGC GTA CTG GAA CCG TTC AAC ATT CGC ATG ATT TGT TAT    1843
Glu Val Phe Gly Val Leu Glu Pro Phe Asn Ile Arg Met Ile Cys Tyr
405                 410                 415                 420

GGC GCA TCC AGC CAT AAC CTG TGC TTC CTG GTG CCC GGC GAA GAT GCC    1891
Gly Ala Ser Ser His Asn Leu Cys Phe Leu Val Pro Gly Glu Asp Ala
                425                 430                 435

GAG CAG GTG GTG CAA AAA CTG CAT AGT AAT TTG TTT GAG TAAATACTGT    1940
Glu Gln Val Val Gln Lys Leu His Ser Asn Leu Phe Glu
            440                 445

ATGGCCTGGA AGCTATATTT CGGGCCGTAT TGATTTTCTT GTCACTATGC TCATCAATAA    2000

ACGAGCCTGT ACTCTGTTAA CCAGCGTCTT TATCGGAGAA TAATTGCCTT TAATTTTTTT    2060

ATCTGCATCT CTAATTAATT ATCGAAAGAG ATAAATAGTT AAGAGAAGGC AAAATGAATA    2120

TTATCAGTTC TGCTCGCAAA GGAATTC                                        2147

(2) INFORMATION FOR SEQ ID NO:8:

(i) SEQUENCE CHARACTERISTICS:
        (A) LENGTH: 449
        (B) TYPE: amino acid
        (D) TOPOLOGY: linear (ii) MOLECULAR TYPE: peptide (xi) SEQUENCE DESCRIPTION: SEQ ID NO:8:

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
    50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Ala Leu Ala Thr Ser Pro Ala Leu Thr Asp
            100                 105                 110

Glu Leu Val Ser His Gly Glu Leu Met Ser Thr Leu Leu Phe Val Glu
    115                 120                 125

Ile Leu Arg Glu Arg Asp Val Gln Ala Gln Trp Phe Asp Val Arg Lys
130                 135                 140
```

```
Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
            165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
            195                 200                 205

Ala Glu Ala Leu His Ala Ser Arg Val Asp Ile Trp Thr Asp Val Pro
210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
                340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
            370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
                405                 410                 415

Met Ile Cys Tyr Gly Ala Ser Ser His Asn Leu Cys Phe Leu Val Pro
                420                 425                 430

Gly Glu Asp Ala Glu Gln Val Val Gln Lys Leu His Ser Asn Leu Phe
            435                 440                 445

Glu
```

(2) INFORMATION FOR SEQ ID NO:9:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULAR TYPE: other..synthetic DNA (xi) SEQUENCE DESCRIPTION: SEQ ID NO:9:

CATCTAAGTA TGCATCTCGG                                                    20

(2) INFORMATION FOR SEQ ID NO:10:

(i) SEQUENCE CHARACTERISTICS:
        (A) LENGTH: 20

```
            (B) TYPE: nucleic acid
            (C) STRANDEDNESS: single
            (D) TOPOLOGY: linear (ii) MOLECULAR TYPE: other..synthetic DNA (xi) SEQUENCE DESCRIPTION: SEQ ID NO:10:

TGCCCCTCGA GCTAAATTAG                                                20

(2) INFORMATION FOR SEQ ID NO:11:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULAR TYPE: other..synthetic DNA (xi) SEQUENCE DESCRIPTION: SEQ ID NO:11:

TTTATTCATA ATTGCCACCG                                                20

(2) INFORMATION FOR SEQ ID NO:12:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULAR TYPE: other..synthetic DNA (xi) SEQUENCE DESCRIPTION: SEQ ID NO:12:

CACGGTAATA CATATAACCG                                                20

(2) INFORMATION FOR SEQ ID NO:13:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULAR TYPE: other..synthetic DNA (xi) SEQUENCE DESCRIPTION: SEQ ID NO:13:

CCTGCAATTG TCAAACGTCC                                                20

(2) INFORMATION FOR SEQ ID NO:14:

(i) SEQUENCE CHARACTERISTICS:
            (A) LENGTH: 20
            (B) TYPE: nucleic acid
            (C) STRANDEDNESS: single
            (D) TOPOLOGY: linear (ii) MOLECULAR TYPE: other..synthetic DNA (xi) SEQUENCE DESCRIPTION: SEQ ID NO:14:

GTCGACGCGC TTGAGATCTT                                                20
```